United States Patent [19]
Nichols et al.

[11] Patent Number: 5,330,513
[45] Date of Patent: Jul. 19, 1994

[54] DIAGNOSTIC FUNCTION DATA STORAGE AND TELEMETRY OUT FOR RATE RESPONSIVE CARDIAC PACEMAKER

[75] Inventors: Lucy M. Nichols, Maple Grove; Glenn M. Roline, Anoka; Tom D. Bennett, Shoreview; David L. Thompson, Fridley, all of Minn.

[73] Assignee: Medtronic, Inc., Minneapolis, Minn.

[21] Appl. No.: 881,996

[22] Filed: May 1, 1992

[51] Int. Cl.$^5$ .............................................. A61N 5/00
[52] U.S. Cl. ....................................... 607/32; 607/17
[58] Field of Search ................. 128/419 PG, 419 DT; 607/14, 15, 17-26

[56] References Cited

U.S. PATENT DOCUMENTS

| | | | |
|---|---|---|---|
| 4,388,927 | 6/1983 | Schober | 128/419 |
| 4,393,874 | 7/1983 | Nappholz et al. | 128/419 |
| 4,428,378 | 1/1984 | Anderson et al. | 128/419 |
| 4,485,813 | 12/1984 | Anderson et al. | 128/675 |
| 4,513,743 | 4/1985 | van Arragon et al. | 128/419 |
| 4,556,063 | 12/1985 | Thompson et al. | 128/419 |
| 4,566,456 | 1/1986 | Koning et al. | 128/419 |
| 4,716,903 | 1/1988 | Hansen et al. | 128/419 |
| 4,726,380 | 2/1988 | Vollmann et al. | 128/419 |
| 4,730,619 | 3/1988 | Koning et al. | 128/419 |
| 4,827,934 | 5/1989 | Ekwall | 128/419 |
| 4,972,834 | 11/1990 | Begemann et al. | 128/419 PG |
| 5,052,388 | 10/1991 | Sivula et al. | 128/419 |
| 5,080,096 | 1/1992 | Hooper et al. | 128/419 |
| 5,117,824 | 6/1992 | Keimel et al. | 607/14 |
| 5,127,404 | 7/1992 | Wyborny et al. | 128/419 |
| 5,154,170 | 10/1992 | Bennett et al. | 128/419 |

Primary Examiner—Lee S. Cohen
Assistant Examiner—Marianne Parker
Attorney, Agent, or Firm—Gregory P. Gadson; Harold R. Patton

[57] ABSTRACT

An implantable physiologic device, e.g., a multi-programmable, microprocessor based cardiac pacemaker, is provided with data storage and transmission capabilities for transmitting out certain current operating parameters and sensed events and for storing counted events for transmission of counts, histograms and real-time clock data out on command. The device preferably comprises a rate responsive cardiac pacemaker for providing an optimized pacing rate of stimulation pulses as a function of at least one selected rate control parameter. Each rate control parameter has a value which varies as a function of changes in a patient's physiologic demand and includes a sensor system for sensing the rate control parameter value and for providing a sensor output representative thereof. The cardiac pacemaker also includes control circuitry which includes a rate response defining means for deriving desired pacing rates as a function of the sensor output signal(s) modified by sensor gain and selective weighting coefficient values. An achievement monitoring means that has a predetermined achievement criterion monitors the relationship between the derived pacing rates and the achievement criterion over an optimization period. Output circuitry providing optimized pacing rates as a function of optimization is accomplished by adjusting the rate response gain for each sensor as a function of the monitored achievement relationship. Another optimization function is provided by adjusting a sensor weighting coefficient value which weights or regulates the relative contribution each sensor's derived desired pacing rates will contribute toward the pacemaker-derived optimized pacing rate.

13 Claims, 19 Drawing Sheets

| OFFSET (decimal) | MAP 1 |
|---|---|
| 0 | PACED RATE PRH HISTOGRAM |
| 30 | NOT USED |
| 38 | SENSED RATE SRH HISTOGRAM |
| 76 | HIST. TIME OF OVERFLOW |
| 79 | NOT USED |
| 105 | PACED EVENT COUNT PEC |
| 108 | SENSE EVENT COUNT SEC |
| 113 | COUNT TIME OF OVERFLOW |
| 116 | PVC COUNT/HIST W/ TIME OF OVERFLOW PVC |
| 127 | OVERFLOW FLAG |

| OFFSET (decimal) | MAP 2 APC |
|---|---|
| 0 | AMPLITUDE OR PULSEWIDTH CHANGES |
| 127 | |

| OFFSET (decimal) | MAP 3 RATE TREND RTA ANALYSIS |
|---|---|
| 0 | RATE AVERAGES |
| 60 | % PACED AVERAGES % PACE |
| 90 | ACT GAINS ; dP/dt GAINS RTA OR COEFFICIENTS GC |
| 101 | NOT USED |
| 105 | PACED EVENT COUNT PEC |
| 108 | SENSE EVENT COUNT SEC |
| 113 | COUNT TIME OF OVERFLOW |
| 116 | PYC COUNT/HIST W/TIME OF OVERFLOW PVC |
| 127 | OVERFLOW FLAG |

| OFFSET (decimal) | MAP 4 OPTIMIZATION OTA TREND ANALYSIS |
|---|---|
| 0 | ACT GAINS ; dP/dt GAINS OR COEFFICIENTS |
| 30 | NOT USED |
| 104 | |
| 105 | PACED EVENT COUNT PEC |
| 108 | SENSE EVENT COUNT SEC |
| 113 | COUNT TIME OF OVERFLOW |
| 116 | PYC COUNT/HIST W/ TIME OF OVERFLOW PVC |
| 127 | OVERFLOW FLAG |

| OFFSET (decimal) | MAP 5 STA SENSING THRESHOLD TREND ANALYSIS |
|---|---|
| 0 | NOT USED |
| 64 | |
| 105 | PACED EVENT COUNT PEC |
| 108 | SENSE EVENT COUNT SEC |
| 113 | COUNT TIME OF OVERFLOW |
| 116 | PYC COUNT/HIST W/ TIME OF OVERFLOW PVC |
| 127 | OVERFLOW FLAG |

| OFFSET (decimal) | MAP 6 PRTA PROJECTED RATE TREND ANALYSIS |
|---|---|
| 0 | NOT USED |
| 60 | |
| 105 | PACED EVENT COUNT PEC |
| 108 | SENSE EVENT COUNT SEC |
| 113 | COUNT TIME OF OVERFLOW |
| 116 | PYC COUNT/HIST W/ TIME OF OVERFLOW PVC |
| 127 | OVERFLOW FLAG |

FIG. 9

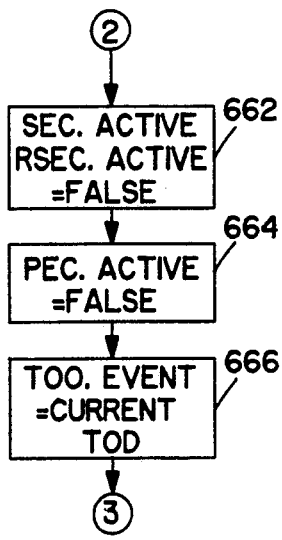
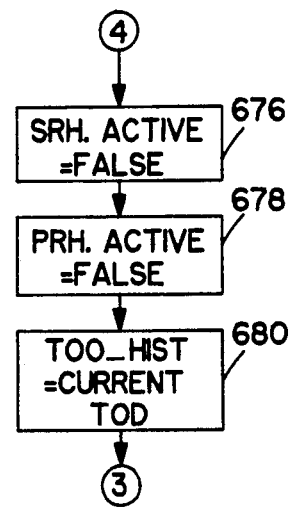
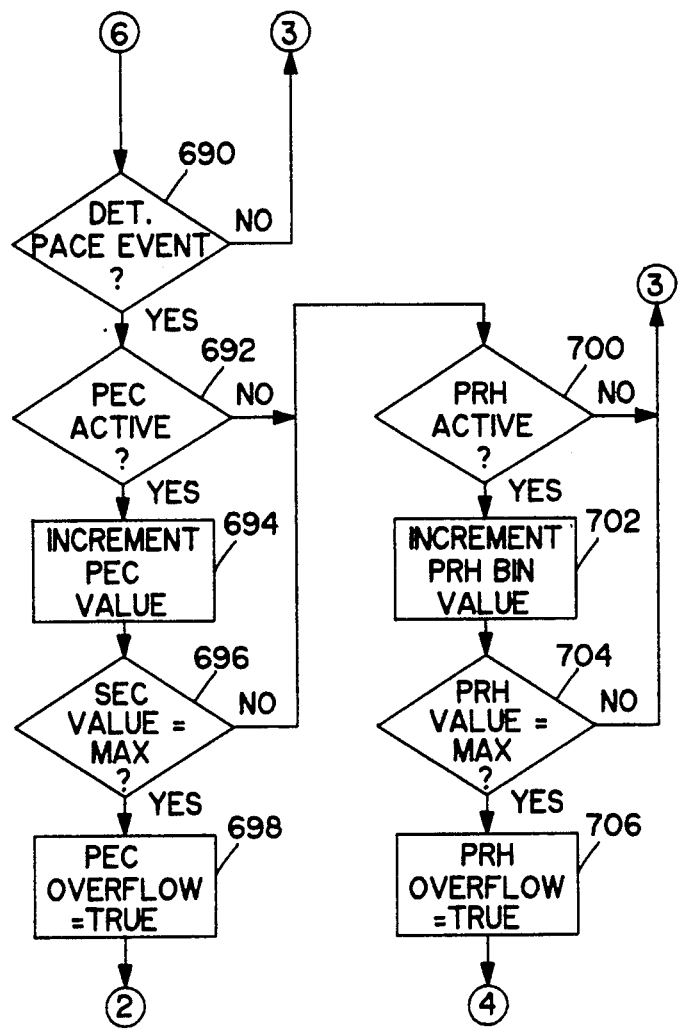
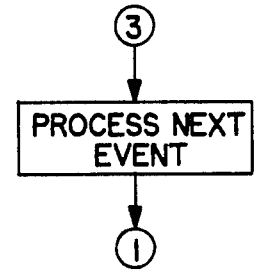
FIG. 11
FIG. 12
FIG. 13
FIG. 13A

DIAGNOSTIC FUNCTION DATA STORAGE AND TELEMETRY OUT FOR RATE RESPONSIVE CARDIAC PACEMAKER

CROSS-REFERENCE TO RELATED APPLICATIONS

Reference is hereby made to commonly assigned, U.S. Pat. No. 5,127,404, issued Jul. 7, 1992 to Paul B. Wyborny, et al., which was based on a continuation application of U.S. Pat. application Ser. No. 468,407, filed Jan. 22, 1990, now abandoned, and also to U.S. Pat. No. 5,154,476, issued Oct. 13, 1992 to Tommy D. Bennett et al., each of which are incorporated by reference in their entireties.

BACKGROUND OF THE INVENTION

1. Field of the Invention

The present invention generally relates to cardiac pacemakers, and more particularly, pertains to cardiac pacemakers of the type which measure physiologic or metabolic requirements and vary the rate of the pacemaker in accordance therewith and store data related to a variety of physiologic sensor data, sensed and paced events, rates, sensitivities, trends, and the like, for telemetry out on command.

2. Description of the Prior Art

Early cardiac pacemakers provided a fixed-rate stimulation pulse generator that could be reset on demand by sensed atrial and/or ventricular depolarizations. Modern pacemakers include complex stimulation pulse generators, sense amplifiers and leads which can be configured or programmed to operate in single or dual chamber modes of operation, delivering pacing stimuli to the atrium and/or ventricle at fixed rates or rates that vary between an upper rate limit and a lower rate limit.

In recent years, single and dual chamber pacemakers have been developed which measure rate control parameters (RCP's) which are directly or indirectly related to metabolic requirements (e.g., demand for oxygenated blood) and vary the pacing rate in response to such measured RCP's. Such RCP's include, for example, physical activity of the body, right ventricular blood pressure and the change of right ventricular blood pressure over time, venous blood temperature, venous blood oxygen saturation, evoked response, respiration rate, minute ventilation, and various pre- and post-systolic time intervals measured by impedance or pressure sensing within the right ventricle of the heart. Such RCP-measuring, sensor-driven pacemakers have been developed for the purpose of restoring rate response to physiologic stress in patients lacking the ability to increase rate adequately by stress.

In general, a rate responsive pacemaker includes a sensor which produces a sensor output representative of a selected RCP, such sensor output varying between a maximum sensor output level and a minimum sensor output level ("Sensor Output"). The pacemaker provides a pacing rate ("Pacing Rate") which typically varies as a linear or monotonic function ("f") of the sensor output between a selectible lower pacing rate ("Lower Rate") and upper pacing rate ("Upper Rate"). Function f has a selectible slope (i.e., Pacing Rate change/Sensor Output change) adjustable by means of an external programmer in conjunction with the Lower and Upper Rates. Thus, the Pacing Rate typically provided is equal to the pre-selected Lower Rate plus an increment which is a function of the measured Sensor Output, as follows:

Pacing Rate=Lower Rate+$f$(Sensor Output).

A human's heart rate, however, is normally controlled by a complex set of inputs to the autonomic nervous system. Consequently, no single type of sensor has been found to be entirely satisfactory for controlling rate response functions. Some of the shortcomings of single-sensor, rate responsive pacemakers, for example, can include: (1) long-term sensor instability, such as from degradation; (2) long-term changes in correlation between sensor output and its RCP being measured, due to physiologic changes in the patient, such as biologic/-sensor interface changes due to tissue changes; (3) changes in sensor sensitivity; and (4) the need for frequent re-programming to accommodate the foregoing problems, as they are encountered.

Various efforts have consequently been made to develop a multiple-sensor pacemaker which is capable of varying its rate as a function of more than one type of measured RCP. Unfortunately, implementation of such multiple sensor-driven rate response concepts has proven to be very difficult and not entirely satisfactory. In addition to those problems listed above as to single-sensor pacemakers, other problems which are typically encountered include: (1) differences between sensors in long-term stability; (2) differences between sensors in immunity to noise; (3) differences in response time to changing metabolic conditions; (4) differences between sensors in correlation between each sensor output and its RCP being measured; and (5) complex set-up procedures, including the need for frequent re-programming.

The enhanced functional capabilities of RCP-measuring, sensor driven process has, together with advances in microprocessor technology, led to the need for and the ability to implement diagnostic data storage of a number of pacing parameters and physiologic event data categories, including the following:

| Stored Data for Telemetry Out | Prior Art |
| --- | --- |
| PVC's (R-sense events) | U.S. Pat. No. 4,388,927 |
| PVC couplets | U.S. Pat. No. 4,388,927 |
| Pace outputs (events) | U.S. Pat. No. 4,388,927 |
| PAC's (P-Sense events) | U.S. Pat. No. 4,388,927 |
| P-Sense events during P-refractory | U.S. Pat. No. 4,388,927 |
| Loss of Capture (LOC) events | U.S. Pat. No. 4,388,927 |
| Noise (R sense) during R-refractory | U.S. Pat. No. 4,388,927 |
| Pacemaker reversions for V & A sense amp. | U.S. Pat. No. 4,388,927 |
| PAC's | U.S. Pat. No. 4,388,927 |
| Trends derived from changes from initial test data stored by physician in RAM reflecting above data parameters | U.S. Pat. No. 4,388,927 |
| Bradycardia pauses | Nappholz U.S. 4,393,874 |
| Rolling or frozen rate versus time histograms (trends) | Medtronic ® ELITE ® pacer |
| P-Sense, R-Sense events | Medtronic ® ELITE ® pacer |
| Sensor events | Medtronic ® ELITE ® pacer |
| Short, medium and long-term data periods | Medtronic ® ELITE ® pacer |
| Rate range histograms in 8 bins | Medtronic ® ELITE ® pacer |
| Times of events (PVCs, PACs) | U.S. Pat. No. 4,513,743 |
| A-V interval histograms | U.S. Pat. No. 4,513,743 |
| Pacing rate or interval histograms | U.S. Pat. No. 4,513,743 |

-continued

| Stored Data for Telemetry Out | Prior Art |
|---|---|
| V-PVC interval histograms | U.S. Pat. No. 4,513,743 |
| Peak QRS amplitude histograms | U.S. Pat. No. 4,513,743 |
| Pace pulse amplitude, width, interval histogram | U.S. Pat. No. 4,513,743 |
| Overflow accumulation of histogram bins | U.S. Pat. No. 4,513,743 |
| Alternate accumulation of "n" histograms ("previous" and "current") over the same period of time | U.S. Pat. No. 4,513,743 |
| Accumulation of histograms for each x hour period of each 24 hour day | U.S. Pat. No. 4,513,743 |
| Sensing threshold | U.S. Pat. No. 4,827,934 |
| Percent pacing over "x" time period or number of events | U.S. Pat. No. 4,726,380 |
| Average rate over "x" time period or number of events | U.S. Pat. No. 4,726,380 |
| Maximum rate over "x" time period or number of events | U.S. Pat. No. 4,726,380 |
| Number of tachycardia episodes over "x" time period or number of events | U.S. Pat. No. 4,726,380 |
| Maximum tachycardia duration over "x" time period or number of events | U.S. Pat. No. 4,726,380 |
| Number of days since implant | U.S. Pat. No. 4,726,380 |
| Number of days since last reprogramming/data read out | U.S. Pat. No. 4,726,380 |
| Patient medical history and medication | U.S. Pat. No. 4,726,380 |
| Programmed parameter values | U.S. Pat. No. 4,726,380 |
| Number of high rate episodes sensed | Intermedics ® Cosmos ® II |
| Duration of high rate episodes sensed | Intermedics ® Cosmos ® II |
| Shortest interval in longest high rate episode | Intermedics ® Cosmos ® II |
| Number of PVCs | Intermedics ® Cosmos ® II |
| Number of A-sense followed by V-sense | Intermedics ® Cosmos ® II |
| Number of A-sense followed by V-pace | Intermedics ® Cosmos ® II |
| Number of A-pace followed by V-sense | Intermedics ® Cosmos ® II |
| Number of A-pace followed by V-pace | Intermedics ® Cosmos ® II |
| Number of times VURL reached | Intermedics ® Cosmos ® II |
| Number of times tachy termination initiated | Intermedics ® Cosmos ® II |
| Stimulation Thresholds | Vitatron Quintech ® TX 915 |
| Short-term rate histogram (frozen bins) | Siemens Sensolog ® 703 |
| Sensor Indicated Rate Histogram (whether or not pacer is inhibited) every 16 seconds distributed in 4 rate bins, all frozen when one bin filled | Siemens Sensolog ® 703 |
| Pace event counter | Siemens Sensolog ® 703 |
| Interference event counter | Siemens Sensolog ® 703 |
| Retrograde P-wave termination attempts | ELA Chorus ® |
| Fallback starts | ELA Chorus ® |
| Number of program changes | ELA Chorus ® |
| Other data/events as listed above | ELA Chorus ® |
| ECG signal slope/changes as time changes | U.S. Pat. No. 4,716,903 |

In the context of such RCP-measuring sensor-driven pacemakers, the storage for telemetry out on command of these and a number of other parameters, falling within the categories of current operating and measured parameter values and cumulative logged data is of importance to physicians. For example, it would be desirable to a physician to know just when certain logged data event and histogram bin counters overflow and data collection is halted. In conjunction with sensing natural cardiac depolarization, i.e. P-sense and R-sense events, it is desirable to track the sensing threshold and develop trend data over time. Where the available RCP sensor is capable of detecting capture, it is desirable to record certain operating parameters upon detection of loss-of-capture (LOC).

SUMMARY OF THE INVENTION

It is thus an object of the present invention to record certain current measured and logged data parameter values of the rate control algorithm of a RCP-measuring, sensor driven pacemaker and other sensed and operating parameters thereof, including trend analysis, projected trend analysis, histograms and time of overflow of histogram bins and other counters for telemetry out on command.

It is further object of the present invention to incorporate the above capabilities in a method and apparatus for automatically optimizing the pacing rate in a rate-responsive cardiac pacemaker as a function of at least one selected rate control parameter (RCP), such that the above-listed problems are better accommodated in a self-adaptive manner. Each RCP has a value which varies as a function of changes in a patient's physiologic demand (such as for oxygenated blood).

The pacemaker of the present invention includes: (1) sensing means for sensing each RCP and for providing a sensor output representative of such RCP value; and (2) control circuitry coupled to sensing means, which includes, in addition to other functions listed below: (a) rate response defining means for deriving desired pacing rates as a function of each sensor output; (b) achievement monitoring means having a predetermined achievement criterion, for monitoring the relationship between the derived desired pacing rates and the achievement criterion over a predetermined optimization period for each sensor; and (c) output means for providing optimized pacing rates as a function of said derived desired pacing rates, or as a function of a sensor weighting coefficient value (described below), and/or as a function of sensor gain optimization activity.

In the preferred embodiment, the pacemaker having two or more sensors provides an optimized pacing rate by performing the sensor gain optimization first, and performing the sensor weighting optimization as a function of the sensor gain optimization activity performed. Following adjustment of both the sensor gains and sensor weighting coefficient at the end of each optimization period, during subsequent optimization periods the desired pacing rates are derived by the control circuitry.

In accordance with the present invention it is contemplated that such a pacemaker may be selectively programmed to acquire, store and transmit two types of data: current values used in automatic control modes; and counts of the cumulative number of events within a set number of events or a period specified by one or more clock. The automatic control values are:

current activity ($S_1$) rate response gain (ACT GAIN),
current dP/dt ($S_2$) rate response gain (PRESS GAIN),
operating and programmed pulse width (PW),
operating and programmed pulse amplitude (PA), and
current sensor weighting coefficient (COEFF).
The types of events counted are:

paced event count (PEC),
paced rate "histogram" (includes paced event at upper rate) (PRH),
sensed event count (includes refractory sensed event counts) (SEC),
sensed rate "histogram" (SRH),
pacing amplitude or pulse width updates (PA, PW METRIC),
rate trend analysis (RTA) with percent paced sensing threshold trend analysis (STA),
projected rate trend analysis (PRTA),
optimization trend analysis (OTA), and
PVC, couplet and run count (PVC CNT).

The read-out of these automatic control values and counted events provides the physician with attractive diagnostic functions or "diagnostics" for understanding the patient's underlying condition and the interaction and efficacy of pacing theories. For example, in several of the event count diagnostics, the time of overflow of an event counter or histogram bin is recorded to provide the physician with an indication of the actual time of overflow to allow correlation to patient activity, to determine the length of time of overflow from the previous follow-up, or ensure that the percent paced calculation is not fooled by the overflow.

In respect to the ACT GAIN, PRESS GAIN and COEFF values, it is desirable to be able to read out not only the current operating values, but sets of trend data which reflect the actual pacing rates against the values over a period of time or number of changes. When one or both of the sensors are programmed OFF it is desirable to be able to provide a similar set of data to provide a diagnosis of how the rate would have varied if the other or both sensors had been programmed ON.

In pacemakers having the capability of detecting the mechanical contraction of the heart it is feasible to detect the loss of capture (LOC) of the heart by a particular pacing pulse energy and to adjust the energy to regain capture ("auto capture"). In this context, diagnostic data of the battery voltage or current and actual and programmed pacing pulse amplitudes and widths over a period of time or events is desirable.

In this and other contexts it is desirable to develop sensing threshold trend diagnostic data to allow optimization of the sensing threshold or to trouble-shoot patient problems.

BRIEF DESCRIPTION OF THE DRAWINGS

The present invention will be better understood, and its attendant advantages will be readily appreciated, by reference to the accompanying drawings when taken in consideration with the following detailed description, wherein:

FIG. 9 are memory maps of the 128 byte buffer in which data of the various counted events diagnostics may be stored;

FIGS. 10-13A are simplified flow charts for storing the sense event count, refractory sense event count, pace event count, sense and pace event histogram and time of overflow algorithms in memory buffer stages illustrated in FIG. 9 (Maps 1, 3-6);

DETAILED DESCRIPTION OF THE PREFERRED EMBODIMENTS

Figure 1:
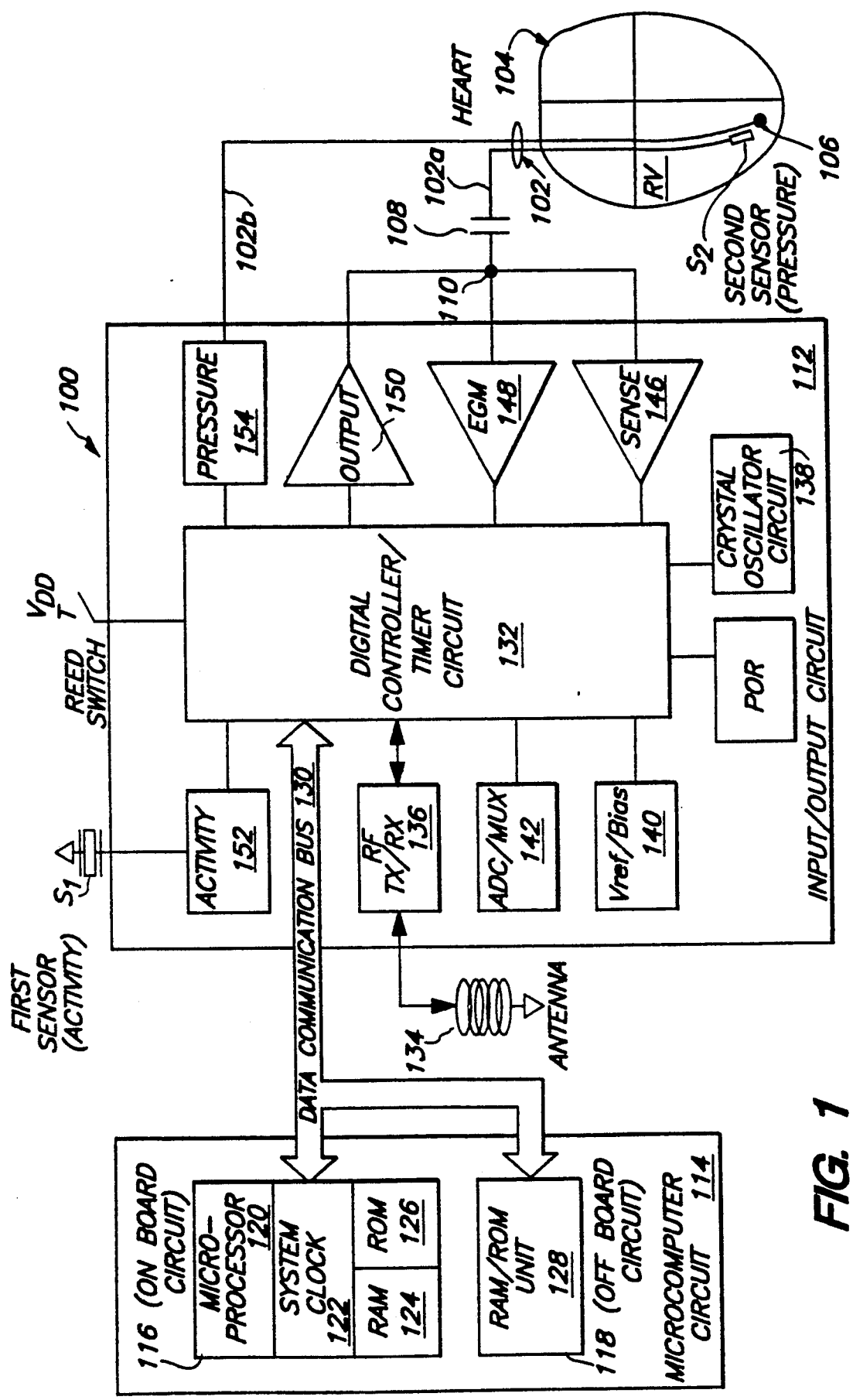
FIG. 1 is a block circuit diagram of a multi-sensor, rate-responsive, implantable, single-chamber, cardiac pacemaker having diagnostic function data storage and telemetry functions according to the present invention.

Part I. Summary of Logged Data Transmissions

The preferred embodiments of the present invention are implemented in the pacemaker described in the above incorporated '476 application preferably employing the uplink telemetry during interrogation described in the above incorporated '407 application, although other known telemetry formats may be employed in the practice of the invention. The following description, in reference to FIGS. 1-5 and Parts II-IX, of the pacemaker and its operating software for adjusting its pacing rate as a function of one or both (depending on the programmed operating mode) of the RCPs, as well as the derivation of correct sensor gain values for each and the weighting coefficient of the equations employed to set the pacing rate is largely repeated from the '476 application. The embodiments of the present invention are set forth in the modification of the algorithm of FIG. 5 (described in PART VIII) and in the remaining figures and parts. The acquisition, storage and telemetry out of these types of data or "diagnostics" is summarized as follows:

A. Current Activity ($S_1$) Rate Response Gain (ACT. GAIN)—When the pulse generator is programmed to use activity rate response in the automatic mode, the programmed activity rate response gain is optimized at 24-hour intervals. The modified value is stored and telemetered upon request.

B. Current dP/dt ($S_2$) Rate Response Gain (PRESS. GAIN)—When the pulse generator is programmed to use dP/dt rate response in the automatic mode, the programmed dP/dt rate response gain is optimized at 24-hour intervals. The modified value is stored and telemetered upon request.

C. Current Sensor Weighting Coefficient (COEFF)—When the pulse generator is programmed with both rate response sensors active and in the automatic mode, the programmed Rate Responsive Sensor Weighting Coefficient may be automatically modified. The modified value is stored and may be telemetered upon request.

D. Pulse Width (PW)—When the pulse generator is programmed to use automatic capture/threshold tracking with stimulus pulse width as the controlling variable, the programmed pulse width will be automatically modified. The modified value is stored and it, along with the current operating pulse width (PW stretching), programmed pulse width, and battery voltage may be telemetered upon request.

E. Pulse Amplitude (PA)—When the pulse generator is programmed to use automatic capture/threshold tracking with the stimulus pulse amplitude as the controlling variable, the programmed pulse amplitude will be automatically modified. The modified value is stored and it, along with the programmed amplitude and battery voltage, may be telemetered upon request.

F. Pace Event Count (PEC)—When this feature is enabled, the pulse generator accumulates a count of all paced events occurring in the window defined by the START TIME and DURATION commands. If programmed to WT, this count may be equivalent to the sensed event count (missing will be sensed events exceeding the rate limit rate). The maximum count is $2^{24}-1$ (167 days @70 ppm). If this counter overflows, the count will be frozen and the time of overflow will be stored. If the sensed event counter is enabled, both counts will be frozen. The count, time of start and overflow, and an indicator identifying which counter has overflowed will be telemetered upon request.

G. Paced Rate "Histogram" (PRH)—When this histogram feature is enabled, the pulse generator accumulates paced rate counts in fifteen bins which are 10 ppm in width, covering the range of 'ppm to 180 ppm, inclusive. Alternatively, these bin limits may be programmed to different values. Counted events must occur in the window defined by the START TIME and DURATION commands. The maximum count in each bin is $2^{16}-1$. If any bin overflows, all counts (and in the Sensed Rate Histogram, if enabled) will be frozen and the time of overflow will be stored. The bin counts, time of overflow and an indicator identifying which counter has overflowed will be telemetered out via uplink telemetry to a programmer peripheral upon request. As structured, this histogram will also provide a count of paced events at the upper rate during WIR modes.

H. Sensed+Refractory Sensed Event Count (SEC+RSEC)—When this feature is enabled, the pulse generator stores counts of all sensed and refractory sensed events occurring in the window defined by the START TIME and DURATION commands. If programmed to VVT, this count may be equivalent to the paced event count. The maximum count is $2^{24}-1$ (167 days @70 bpm) for sensed events and $2^{16}-1$ for refractory sensed events. If either counter overflows, both counts and the paced event counter, if enabled, will be frozen and the time of overflow will be stored. The count, time of start and overflow, and an indicator identifying which counter has overflowed will be telemetered upon request.

I. Sensed Rate "Histogram" (SRH)—When this histogram feature is enabled, the pulse generator accumulates sensed event rate counts in eighteen bins which are 10 bpm in width, covering the range of 40 bpm to 220 bpm, inclusive and a nineteenth bin counting sensed events between 220 bpm and the programmed refractory interval. Alternatively, these bin limits may be programmed to different values. Bin accumulation is impacted by the programmed refractory interval. Only intervals begun by paced events or sensed events and ended by sensed events (non-refractory events) shall be counted. Counted events must occur in the window defined by the START TIME and DURATION commands. The maximum count in each bin is $2^{16}-1$. If any bin overflows, all counts (and the Paced Rate Histogram, if enabled) will be frozen and the time of overflow will be stored. The bin counts, time of overflow, and an indicator identifying which counter had overflowed will be telemetered upon request.

J. Pacing Amplitude and Pulse Width Updates (PA METRIC/PW METRIC)—When this feature is enabled (via START TIME and a duration of six months), the last 32 value changes (due to loss of capture) of the programmed metric are recorded along with the time of change and the current battery voltage (at the time of change). The value recorded is the "measured" (stretched) value being changed from. The time value recorded will be the value of the diagnostic duration (down) counter, at the time of the change, divided by four. This will result in a time of change resolution of four minutes. The values and time of occurrence may be telemetered upon request.

K. PVC Count/Histogram (PVC)—When this feature is enabled, the pulse generator accumulates a count of all premature sensed events as defined by PVC trigger and count parameters, occurring in the window defined by the START TIME and DURATION commands. This function counts the single PVCs, couplets, triplets, runs of four or more PVCs in four dedicated counters. An event's (sensed only) length is compared against the running average of the last eight rhythmic cycles (sensed and paced). If the event length is less than or equal to a programmed percentage less than the mean cycle length, a PVC has been detected. At the end of a run (from 1 to 4, or more PVCs), one of the PVC counters is incremented, i.e. either the single PVC counter, the couplet counter, the triplet counter or the four or more PVCs counter. The four or more PVCs counter is limited to four PVCs detected sequentially. Additional PVCs following the first four are ignored. Each counter has a maximum count of $2^{16}-1$. If one counter overflows, all counters will be frozen and the time of start and overflow will be stored. The count, time of overflow, and an indicator identifying which counter has overflowed will be telemetered upon request.

The pulse generator may permanently be programmed to enable PVC Detection. An event meeting the PVC detection criteria will increment one of the PVC histogram counters. PVC detection requires sensed events to occur earlier than a programmable percentage of an average interval. A sensed event is compared to a programmable percentage prematurity of the running average of the last eight paced or sensed events. A refractory sensed event is not added to the running average nor is it considered to be a valid PVC.

L. Rate Trend Analysis/Rate and Percent Paced Trend (RTA)—When this trend analysis feature is enabled (via START TIME), the pulse generator monitors the pacing rate (averaged), percentage paced, activity rate response gain, dP/dt rate response gain, and rate response sensor coefficient over a programmed time DURATION. The two gain values and sensor coefficient are limited to 0 stored value for the 1-hour run time, one stored value for the 1-day run time, five stored values for the 5-day run time, and ten stored values for the 10-day run time. The information can then be used by a peripheral to plot rate versus time and percentage paced versus rate. The time intervals for calculating averages are selected as follows:

| Total Time | Resolution | Sampling Rate |
| --- | --- | --- |
| 1 Hour | 60 (1-minute segment) | Beat by Beat |
| 1 Day | 60 (32-minute segments) | Beat by Beat |
| 5 Day | 60 (128-minute segments) | Beat by Beat |
| 10 Day | 60 (256-minute segments) | Beat by Beat |

The percentage paced value is stored in the following ranges:

| Range | % Paced Range | Range | % Paced Range |
| --- | --- | --- | --- |
| 0 | 0 < 6.25 | 8 | 50 < 56.25 |
| 1 | 6.25 < 12.5 | 9 | 56.25 < 62.5 |
| 2 | 12.5 < 18.75 | 10 | 62.5 < 68.75 |
| 3 | 18.75 < 25 | 11 | 68.75 < 75 |
| 4 | 25 < 31.25 | 12 | 75 < 81.25 |
| 5 | 31.25 < 37.5 | 13 | 81.25 < 87.5 |
| 6 | 37.5 < 43.75 | 14 | 87.5 < 93.75 |
| 7 | 43.75 < 50 | 15 | 93.75 < 100 |

M. Sensing Threshold Trend Analysis (STA)—When this trend analysis feature is enabled (via START TIME), the pulse generator monitors the average peak sense value over a programmed time interval. The information can then be used by a peripheral to analyze the sensing threshold trends versus time. If less than 32 nonrefractory sensed events occur during sampled segments (1–4096 minutes), the average for that segment will be zero. The time intervals are selected as follows:

| Total Time | Resolution | Sampling Rate |
| --- | --- | --- |
| 1 Hour | 60 (1-minute segment) | Beat by Beat |
| 1 Day | 60 (32-minute segments) | 4 sec |
| 5 Day | 60 (128-minute segments) | 4 sec |
| 10 Day | 60 (256-minute segments) | 4 sec |
| 6 Months | 64 (4,096-minute segments) | 4 sec |

N. Projected Rate Trend Analysis/Sensor Rate Trend (PRTA)—When this trend analysis feature is enabled (via START TIME), the pulse generator monitors the projected rate response pacing rate based upon one or both rate response sensors, the activity rate response gain, dP/dt rate response gain and rate response sensor coefficient. The data format is identical to the rate trend analysis (see L. above) with the deletion of the percentage paced values and the sampling rate changed to two seconds. Optimization does not modify the Projected Rate Trend Analysis. The information may be telemetered to a programmer peripheral to plot rate versus time to enable mode change and parameter optimization. The lower rate used in the projection is the permanently programmed Lower Rate value.

O. Optimization Trend Analysis (Rate Response Trend) (OTA)—When this feature is enabled (via START TIME), the pulse generator monitors the rate responsive gain (activity and/or dP/dt) and sensor coefficient changes over a programmed time interval. The last 52 changes in gain or sensor coefficient will be saved as well as the day (relative to the start of the diagnostic) the changed occurred. The information can then be used by a peripheral to analyze the rate responsive gain trends over time. The specific details of how this data is stored and telemetered out will be described following the description of the rate-responsive pacemaker in PARTS II-IX.

Part II. Description of Pacemaker Device

FIG. 1 is a block circuit diagram illustrating a multi-programmable, implantable, single-chamber, bradycardia pacemaker 100 with multi-sensor rate variability and automatic rate response optimization according to the present invention. Although the present invention is described in conjunction with a microprocessor-based architecture, it will be understood that it could be implemented in digital logic-based, custom IC architecture, if desired. It will also be understood that the present invention may be implemented in dual-chamber pacemakers.

In the preferred embodiment of FIG. 1, pacemaker 100 includes two sensors, namely, $S_1$ and $S_2$, each of which provide a sensor output which varies as a function of a measured parameter that relates to the metabolic requirements of the patient. Since each sensor output can be utilized by pacemaker 100 to control its pacing rate, each sensor output is herein referred to as a rate-control parameter (RCP). Examples of an RCP include, for example, physical activity of the body, right ventricular blood pressure and the change of right ventricular blood pressure over time, venous blood temperature, venous blood oxygen saturation, respiration rate, minute ventilation, and various pre and post-systolic time intervals measured by impedance or pressure sensing within the right ventricle of the heart.

In the preferred embodiment, first sensor $S_1$ comprises an activity sensor, such as a piezoelectric sensor of the type disclosed in U.S. Pat. No. 4,428,378 issued to Anderson et al, entitled "Rate Adaptive Pacer", which is held by the same assignee as the present invention and which is incorporated herein by reference. First sensor $S_1$ thus measures a rate-control parameter related to physiologic forces associated with body activity ($RCP_{act}$), and provides a first sensor output ($Output_{act}$) which is proportional to the patient's activity. Also in the preferred embodiment second sensor $S_2$ comprises a dynamic pressure sensor, such as the type disclosed in U.S. Pat. No. 4,485,813 issued to Anderson et al., entitled "Implantable Dynamic Pressure Transducer System" which is held by the same assignee as the present invention and which is incorporated herein by reference. Second sensor $S_2$ thus measures a rate-control parameter related to changes in fluid pressure in the heart associated with its mechanical activity and contractility ($RCP_{press}$), and provides a second sensor output ($Output_{press}$) which is proportional to the magnitude of the change in fluid pressure in the patient's heart. In the preferred embodiment, second sensor output $S_2$ is processed to derive a peak positive time derivative of the fluid pressure applied to the pressure sensor $S_2$ within the right ventricle of the patient's heart (i.e., $dP/dt_{max}$).

Pacemaker 100 is schematically shown electrically coupled via a pacing lead 102 to a patient's heart 104. Lead 102 includes an intracardiac electrode 106 and second sensor $S_2$ which are located near the distal end of lead 102 and positioned within the right ventricle (RV) of the patient's heart. Lead 102 can carry either unipolar or bipolar electrodes as is well known in the art. In the preferred embodiment, the lead 102 which couples pacemaker 100 to the ventricular endocardium can comprise a steroid-tipped, unipolar lead with an integral pressure transducer of the type described above. Electrode 106 is coupled via suitable lead conductor 102a through output capacitor 108 to node 110 and to input/output terminals of an Input/Output Circuit shown at block 112. Output from first sensor $S_1$ is coupled to Input/Output Circuit 112. Output from second sensor $S_2$ is also coupled to Input/Output Circuit 112 via suitable lead conductor 102b.

Input/Output Circuit 112 contains the operating input and output analog circuits for digital controlling and timing circuits necessary for the detection of electrical signals derived from the heart, such as the cardiac electrogram, output from the first sensor output $S_1$, and output from the second sensor output $S_2$, as well as for the application of stimulating pulses to the heart to control its rate as a function thereof under the control of software-implemented algorithms in a Microcomputer Circuit shown at 114.

Microcomputer Circuit 114 comprises an On-Board Circuit 116 and an Off-Board Circuit 118. On-Board Circuit 116 includes a microprocessor 120, a system clock 122, and on-board RAM 124 and ROM 126. Off-Board Circuit 118 includes an off-board RAM/ROM Unit 128. Microcomputer Circuit 114 is coupled by Data Communication Bus 130 to a Digital Controller/Timer Circuit shown at 132. Microcomputer Circuit 114 may be fabricated of custom IC devices augmented by standard RAM/ROM components.

It will be understood that the electrical components represented in FIG. 1 are powered by an appropriate implantable-grade battery power source (not shown).

An antenna 134 is connected to Input/Output Circuit 112 for purposes of uplink/downlink telemetry through an RF Transmitter/Receiver Circuit (RF TX/RX) shown at 136. Telemetering both analog and digital data between antenna 134 and an external device, such as an external programmer (not shown), is accomplished in the preferred embodiment by means of all data first being digitally encoded and then pulse position modulated on a damped RF carrier, as substantially described in co-pending U.S. patent application Ser. No. 468,407, filed on Jan. 22, 1990, entitled "Improved Telemetry Format", which is held by the same assignee as the present invention and which is incorporated herein by reference.

A Crystal Oscillator Circuit 138, typically a 32,768 Hz crystal-controlled oscillator, provides main timing clock signals to Digital Controller/Timer Circuit 132. A Vref/Bias Circuit 140 generates a stable voltage reference and bias currents for the analog circuits of Input/Output Circuit 112. An ADC/Multiplexor Circuit (ADC/MUX) 142 digitizes analog signals and voltages to provide telemetry and replacement time-indicating function (EOL). A Power-on-Reset Circuit (POR) 144 functions as a means to reset circuit and related functions to a default condition upon detection of a low battery condition, which will occur upon initial device power-up or transiently occur in the presence of electromagnetic interference, for example.

The operating commands for controlling the timing of the pacemaker depicted in FIG. 1 are coupled by bus 130 to Digital Controller/Timer Circuit 132 wherein digital timers set the overall escape interval of the pacemaker, as well as various refractory, blanking and other timing windows for controlling the operation of the peripheral components within Input/Output Circuit 132.

Digital Controller/Timer Circuit 132 is coupled to a sense amplifier (SENSE) 146 and an electrogram amplifier (EGM) 148 for receiving amplified and processed signals picked up from electrode 106 through lead conductor 102a and capacitor 108 representative of the electrical activity of the patient's heart 104. SENSE amplifier 146 produces a sense event signal for re-setting the escape interval timer within Circuit 132. The electrogram signal developed by EGM amplifier 148 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", which is held by the same assignee as the present invention and which is incorporated by herein by reference. An output pulse generator 150 provides the pacing stimulus to the patient's heart 104 in response to a paced trigger signal developed by Digital Controller/Timer Circuit 132 each time the escape interval times out, or an externally transmitted pacing command has been received, or in response to other stored commands as is well known in the pacing art.

Digital Controller/Timer Circuit 132 is coupled to a processing/amplifying circuit (ACTIVITY) 152 for receiving amplified and processed sensor output (Output$_{act}$) from first sensor $S_1$ and associated ACTIVITY circuitry which is representative of activity. Digital Controller/Timer Circuit 132 is coupled to a processing/amplifying circuit (PRESSURE) 154 for receiving amplified and processed sensor output (Output$_{press}$) from second sensor $S_2$ through lead conductor 102$b$ representative of changes in fluid pressure in the patient's heart 104, for use in rate response control, and others functions as desired.

In a preferred embodiment of the present invention, pacemaker 100 is capable of operating in various non-rate-responsive modes which include VVI, VOO and VVT, as well as corresponding rate-responsive modes of VVIR, VOOR and VVTR. Further, pacemaker 100 can be programmably configured to operate such that it varies its rate only in response to one selected sensor output, or in response to both sensor outputs, if desired (i.e., utilizing either or both of Output$_{act}$ or Output$_{press}$).

Part III. Definitions

For purposes of describing the operation of the pacemaker depicted in FIG. 1, a definition of additional relevant terms follows:

Achievement Count (ACH.COUNT)—A measure of the attainment of an Achievement Criterion (ACH.-CRITERION) by the Sensor Target Rate (STR) associated with each RCP-measuring sensor over a predetermined time interval which comprises the Optimization Period (OPT.PERIOD).

Achievement Criterion (ACH.CRITERION)—A value supplied by the clinician which sets an attainment threshold for each Sensor Target Rate (STR) associated with each sensor. This threshold comprises a rate component (Achievement Rate) and a time component (Achievement Duration). The Achievement Rate is a programmable percentage of the difference between the Lower Rate (LR) and the Upper Rate (UR). The Achievement Duration is a minimum time interval over which the Sensor Target Rate must exceed the Achievement Rate. With rate response, the allowed programmable values for ACH.CRITERION range from 70 ppm to 175 ppm at 1 ppm intervals, and the Achievement Duration in the preferred embodiment is fixed at a four-second interval.

Activity Count (ACT.COUNT)—A measure of the output of the activity sensor (Output$_{act}$) over a predetermined interval of time. In the preferred embodiment, each event in which the amplitude of Output$_{act}$ exceeds a predetermined Activity Threshold (ACT.THRESH) is counted over a two-second period and retained. ACT.COUNT is updated every two-second cycle, and its aggregate value comprising the count value accumulated at the end of 3 two-second cycles (i.e., after 6 seconds) is used to calculate the Sensor Target Rate for activity (STR$_{act}$).

Activity Rate Response Gain (ACT.GAIN)—A setting which corresponds to the slope of the function correlating the activity-based Sensor Target Rate (STR$_{act}$) to a value (ACT.COUNT) which corresponds to the activity sensor output (Output$_{act}$). The setting for ACT.GAIN, sometimes alternately referred to as the "activity sensor gain", corresponds to a particular rate response curve (RR). With rate response, the allowed programmable values for ACT.GAIN range from 1 to 10 at setting intervals of 1 (i.e., from RR1 to RR10).

Activity Response Time Acceleration Constant (ACT.ATTACK.TC)—A value which restricts the rate at which the activity-based Sensor Target Rate (STR$_{act}$) rate can increase, such that an activity "attack" curve provides for a more gradual and physiologically appropriate change in pacing rate. In the preferred embodiment, these time values represent the time required to reach 90% of the difference between a first steady-state activity-driven pacing period (constant activity signal input for at least a six-second interval) and a second, shorter, steady-state, activity-driven pacing period when a step increase in activity level occurs. With rate response, the allowed programmable values for ACT.ATTACK.TC are selected from those of 0.25 minutes, 0.5 minutes, or 1.2 minutes.

Activity Response Time Deceleration Constant (ACT.DECAY.TC)—A value which restricts the rate at which the activity-based Sensor Target Rate (STR$_{act}$) can decrease, such that an activity "decay" curve provides for a more gradual and physiologically appropriate change in pacing rate. In the preferred embodiment, these time values represent the time required to reach 90% of the difference between a first steady-state activity-driven pacing period (constant activity signal input for at least a six-second interval) and a second, longer, steady-state, activity-driven pacing period when a step decrease in activity level occurs. With rate response, the allowed programmable values for ACT.DECAY.TC are selected from those of 2.5 minutes, 5 minutes, or 10 minutes.

Activity Threshold (ACT.THRESH)—A minimum value which the amplitude of the activity sensor output (Output$_{act}$) must exceed to serve as input to the rate determination algorithm. The higher the threshold, the greater the amplitude necessary to become an event counted in the Activity Count (ACT.COUNT). With rate response, the allowed programmable values for ACT.THRESH range from low, medium low, medium, medium high, and high.

Lower Rate (LR)—A value supplied by the clinician which establishes a lower boundary on the pacing rate. If the sensors are disabled, or their sensor outputs are not large enough to increase rate, the lower rate is the stimulus rate. With rate response, the allowed programmable values for LR range from 40 ppm to 100 ppm at 1 ppm intervals.

Optimization Period (OPT.PERIOD)—A predetermined time interval, after which the pacemaker 100 performs its optimization of each sensor's rate response (ACT.GAIN or PRESS.GAIN) and Weighting Coefficient (COEFF), based upon the ACH.COUNT value relative to the OPT.RANGE at the expiration of each OPT.PERIOD. In the preferred embodiment, the OPT.PERIOD is established to be a twenty-four hour period.

Optimization Range (OPT.RANGE)—A range determined by the pacemaker 100 as a function of a value (Achievement Index) supplied by the clinician, which defines a minimum value (OPT.RANGE.MIN) and a maximum value (OPT.RANGE.MAX) for the Achievement Count (ACH.COUNT) during each Optimization Period (OPT.PERIOD). With rate response, the allowed programmable values for Achievement Index range from 3 to 8 at setting intervals of 1. In the preferred embodiment, pacemaker 100 determines OPT.RANGE by calculating the minimum value (OPT.RANGE.MIN) by subtracting 2 from the Achievement Index and its maximum value (OPT.RANGE.MAX) by adding 2 to the Achievement Index. Optimization for each sensor's rate response (ACT.GAIN or PRESS.GAIN) and Weighting Coefficient (COEFF) are performed by pacemaker 100 based upon the ACH.COUNT value relative to the OPT.RANGE at the expiration of each OPT.PERIOD.

Optimized Pacing Rate (OPR)—The rate at which the pacemaker 100 is to provide stimulus pulses, which is derived by pacemaker 100 based upon the Sensor Pacing Rates ($SPR_{act}$ and $SPR_{press}$) and the Weighting Coefficient (COEFF), based upon Equation 1 hereinbelow described in Part III.

Pressure (dP/dt) Average (PRESS.AVG)—Dynamic pressure sensor $S_2$ is disposed in the right ventricle (RV) of the patient's heart to sense fluid pressure therein ($RCP_{press}$), and to provide a sensor output ($Output_{press}$) related to changes in the fluid pressure associated with the heart's mechanical activity and contractility. Processing by pacemaker 100 of $Output_{press}$ yields a peak positive first time derivative thereof ($dP/dt_{max}$) which is proportional to the magnitude of such RV pressure changes. Each sensed or paced RV event will yield a peak positive $dP/dt_{max}$ signal, although a peak negative signal may be used as an alternative. In the preferred embodiment, the last 8 valid $dP/dt_{max}$ values are used to determine an average $dP/dt_{max}$ value, referred to as the "Pressure (dP/dt) Average" or "PRESS.AVG". Pacemaker 100 tests for validity of each $dP/dt_{max}$ value on a sample-by-sample basis, based upon the requirement that a sampled $dP/dt_{max}$ value must be within a predetermined range defined by a $dP/dt_{max}$ value (REST.PRESS) associated with the patient's Resting Rate (REST.RATE). In the preferred embodiment, this validity range is defined as $dP/dt_{max}$ values between 25% to 400% of REST.PRESS. Values outside this validity range are ignored. Once determined, PRESS.AVG is used to calculate the pressure-based Sensor Target Rate-($STR_{press}$) on a cycle-to-cycle basis or once upon request, according to Equation 3 hereinbelow set forth.

Pressure (dP/dt) Rate Response Gain (PRESS.GAIN)—A setting which corresponds to the slope of the function correlating the pressure-based Sensor Target Rate ($STR_{press}$) to a value (PRESS.AVG) which corresponds to the pressure sensor output ($Output_{press}$). The setting for PRESS.GAIN, sometimes alternately referred to as the "pressure sensor gain" or "dP/dt sensor gain" corresponds to a particular rate response curve (RR). With rate response, the allowed programmable (permanent) values for PRESS.GAIN range from 1 to 10 at setting intervals of 1 (i.e., from RR1 to RR10).

Pressure (dP/dt) Response Time Acceleration Constant (PRESS.ATTACK.TC)—A value which restricts the rate at which the pressure-based Sensor Target Rate ($STR_{press}$) can increase, such that a pressure "attack" curve provides for a more gradual and physiologically appropriate change in pacing rate. In the preferred embodiment, this time value represents the time required to reach 90% of the difference between a first steady-state, pressure-driven pacing period (constant $dP/dt_{max}$ signal input for at least 8 events) and a second, shorter, steady-state, pressure-driven pacing period when a step increase in $dP/dt_{max}$ level occurs. With rate response, PRESS.ATTACK.TC has a fixed value of 0.25 minutes.

Pressure (dP/dt) Response Time Deceleration Constant (PRESS.DECAY.TC)—A value which restricts the rate at which the pressure-based Sensor Target Rate ($STR_{press}$) can decrease, such that a pressure "decay" curve provides for a more gradual and physiologically appropriate change in pacing rate. In the preferred embodiment, this time value represents the time required to reach 90% of the difference between a first steady-state, pressure-driven pacing period (constant $dP/dt_{max}$ signal input for at least 8 events) and a second, longer, steady-state, pressure-driven pacing period when a step decrease in $dP/dt_{max}$ level occurs. With rate response, PRESS.DECAY.TC has a fixed value of 0.25 minutes.

Resting (dP/dt) Pressure (REST.PRESS)—The arithmetic mean of the pressure-based signal of interest (peak positive dP/dt values or $dP/dt_{max}$) measured during a predefined time interval with the patient at rest (i.e., the representative $dP/dt_{max}$ value which correlates REST.RATE).

Resting Rate (REST.RATE)—A rate identified by the clinician during initialization for later use in the pressure-based pacing mode comprising the arithmetic mean of paced or intrinsic rates measured over a predefined time interval with the patient at rest. In the preferred embodiment, the allowed programmable values for REST.RATE range from 40 ppm to 100 ppm at 5 ppm intervals.

Sensor Pacing Rate (SPR)—The rate calculated by the pacemaker 100 in conjunction with each sensor based upon its respective Sensor Target Rate (STR) and the contribution thereto based upon its respective acceleration and deceleration function.

Sensor Target Rate (STR)—The rate calculated by the pacemaker 100 in conjunction with each sensor based upon programmed settings and the respective sensor output. STR does not take into account the effect which the acceleration and deceleration function produce on the Sensor Pacing Rate (SPR).

Upper Rate (UR)—A value supplied by the clinician which limits the maximum stimulation rate when the rate responsive modes for activity, pressure, or both combined, are in effect, such that the sensor-driven pacing rate generated by pacemaker 100 does not become hemodynamically excessive. With rate response, the allowed programmable values range from 100 ppm to 175 ppm at 5 ppm intervals, provided UR must also be at least 20 ppm greater than Lower Rate (LR) and Resting Rate (REST.RATE).

Weighting Coefficient (COEFF)—In a rate-response pacing mode wherein both sensors (i.e., more than one sensor) are enabled, the "Weighting Coefficient" establishes the proportion or weight of control given to each Sensor Pacing Rate (SPR) in deriving a fully-optimized rate (Optimized Pacing Rate) at which the pacemaker 100 should provide stimulus pulses (OPR). After each STR has been calculated as an intermediate rate control value from its respective Sensor Target Rate (STR), the coefficient is used in a weighting equation as a form of gain multiplier to regulate the emphasis placed on each STR in order to derive the Optimized Pacing Rate (OPR) at which the pacemaker 100 can deliver stimulus pulses. In the preferred embodiment, an OPR is calculated as follows:

$$OPR = [(1 - COEFF) * SPR_{act} + (COEFF * SPR_{press})] \quad \text{(Equation 1)}$$

During initialization by the programmer, a Programmed Coefficient Value (COEFF$_{PROG}$) is also assigned by the programmer, such as a value of 0.5, to which pacemaker 100 will automatically default upon the occurrence of certain events encountered during an optimization procedure, as hereinbelow described. In the preferred embodiment, the allowed programmable values for COEFF range from 0 to 1.0 at interval settings of 0.125. During an optimization cycle at the end of the OPT.PERIOD, pacemaker 100 can automatically adjust COEFF by a step increment or decrement of 0.125, or in larger increments or decrements in a single optimization cycle under certain conditions hereinbelow described.

Part IV. Sensors

A brief description of measurement of the rate control parameter for activity (RCP$_{act}$) now follows. The activity sensor S$_1$ sensor employed is a piezoelectric crystal transducer of the type described in the above-mentioned '378 Anderson et al. patent, which is mounted to the interior surface of the pacemaker can as disclosed therein. Sensor S$_1$ generates a sensor output (Output$_{act}$) due to deflection of the pacemaker can as a result of compression waves within the body caused by physical movement of the body. Processing by ACTIVITY circuit 152 is performed, such that each event in which the amplitude of Output$_{act}$ exceeds a programmed Activity Threshold (ACT.THRESH) is then counted and retained in an Activity Count (ACT.COUNT) of pacemaker 100. ACT.COUNT is used to calculate the activity-based Target Rate (STR$_{act}$) on a cycle-to-cycle basis, according to Equation 2 hereinbelow set forth in Part V.

A brief description of measurement of the rate control parameter for pressure (RCP$_{press}$) now follows. The pressure sensor S$_2$ sensor employed is a dynamic pressure sensor of the type described in the above-mentioned '813 Anderson et al. patent. Sensor S$_2$ is disposed in the right ventricle (RV) of the patient's heart to sense fluid pressure therein (RCP$_{press}$), and to provide a sensor output (Output$_{press}$) related to changes in the fluid pressure associated with the heart's mechanical activity and contractility. Processing by PRESSURE circuit 154 of Output$_{press}$ yields a peak positive first time derivative thereof (dP/dt$_{max}$) which is proportional to the magnitude of such RV pressure changes. Each sensed or paced RV event will yield a peak positive dP/dt$_{max}$ signal, although a peak negative signal may be used as an alternative. In the preferred embodiment, the last 8 valid dP/dt$_{max}$ values are used to determine an average dP/dt$_{max}$ value, referred to as the "Pressure (dP/dt) Average" or "PRESS.AVG". Pacemaker 100 tests for validity of each dP/dt$_{max}$ value on a sample-by-sample basis, based upon the requirement that a sampled dP/dt$_{max}$ value must be within a predetermined range defined by a dP/dt$_{max}$ value (REST.PRESS) associated with the patient's Resting Rate. (REST.RATE). In the preferred embodiment, this validity range is defined as dP/dt$_{max}$ values between 25% to 400% of REST.PRESS. Values outside this validity range are ignored. Once determined, PRESS.AVG is used to calculate the pressure-based Sensor Target Rate (STR$_{press}$) on a cycle-to-cycle basis, according to Equation 3 hereinbelow set forth in Part V.

It will be understood, however, that the present invention can be practiced with more than two sensors, or with sensors of a type other than the ones above described. In the preferred embodiment, however, various advantages are obtained by the use of the particular sensors in the specific combination stated above.

For example, an activity-based sensor provides a fast and repeatable response to physical activity. Sensors of this type have been exhaustively reported in clinical literature, and their safety and efficacy are well-documented. Additionally, such sensors offer the advantage of being less affected by changes in a patient's health or disease status, and thus provide more predictable behavior over time. However, there are also theoretical and practical limitations to the behavior of activity sensors. For example, they respond only to physical activity. Therefore, patients undergoing other types of physiological stresses which would normally evoke a heart rate response, such as thermal stress associated with normal exposure to wide variations in ambient temperature, or postural stress associated with changing from lying down to erect position, will tend to obtain only very limited rate adjustment and their adjustment to such stresses will thus be less than entirely adequate. Additionally, the time course of rate recovery after an activity event tends to be limited by the design constraints of the pacemaker system which are not generally capable of providing a highly physiologically-based recovery function.

Consequently, the preferred embodiment also incorporates a dynamic pressure sensor for continuous measurement of cardiac pressures on a beat-by-beat basis. This sensor provides for more physiological responses than activity alone, and helps to complement the rate response provided by the activity sensor. The sensed physiologic variable in this system comprises the rate of increase in pressure within the right ventricle of the heart (i.e., a peak positive dP/dt). This variable is related to the vigor of contraction of the cardiac muscle, which in turn is regulated by the autonomic nervous system. Thus, any stress which elicits a response by the autonomic nervous system in the patient (and would cause a heart rate response in a normal individual), will also yield a heart rate response in the patient by means of the pacemaker system of the present invention. Additionally, the time course of recovery of the cardiac pressure following stresses follows the physiologic time course determined by the status of the autonomic nervous system, such that the present device will provide for pacing rate recovery which is more physiological than that which can be provided by activity sensors alone.

It can thus be appreciated that the particular sensor combination described above yields significantly improved rate response function for pacemaker 100.

Part V. Rate Response (Sensor Gain) Curves

Figure 2A:
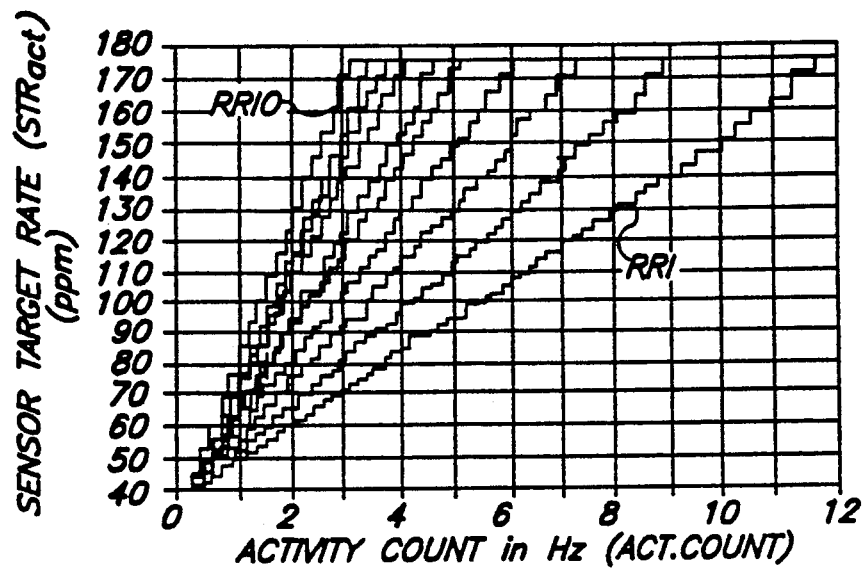
FIG. 2A is a graph illustrating multiple rate response curves correlating an output derived from a first sensor (which measures an activity-based rate control parameter) with a target pacing rate (calculated as a function of such first sensor output)
Figure 2B:
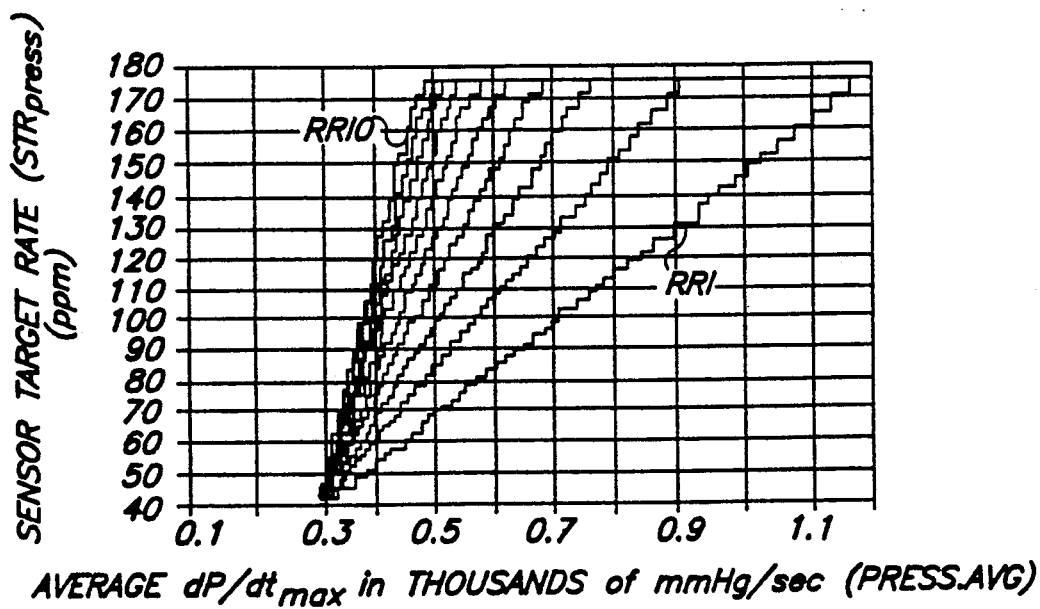
FIG. 2B is a graph illustrating multiple rate response curves correlating an output derived from a second sensor (which measures a pressure-based rate control parameter) with a target pacing rate (calculated as a function of such second sensor output)

FIGS. 2A and 2B each graphically illustrate examples of a family of rate response curves for the first and second sensors S$_1$ and S$_2$, respectively. The horizontal axes of each graph correspond to sensor output values being measured. In FIG. 2A, the metric for the horizontal axis corresponds to an activity-based rate control parameter (RCP$_{act}$) and comprises the Activity Count (ACT.COUNT) as defined above, which is a function of Output$_{act}$, expressed in counts per second (Hz). In FIG. 2B, the metric for the horizontal axis corresponds to a pressure-based rate control parameter (RCP$_{press}$)

and comprises the average $dP/dt_{max}$ value determined (PRESS.AVG) as defined above, which is a function of Output$_{press}$, expressed in thousands of mmHg per second. The vertical axes of each graph correspond to a Sensor Target Rate (STR), expressed in pulses per minute (ppm).

It can be seen that the Sensor Target Rate (STR) for each sensor is thus a function of the respective sensor's output, which functional correlation is defined in more detail hereinbelow. These Sensor Target Rates are utilized by pacemaker 100 in deriving the rate-responsive pacing rate for the patient's heart.

Ten rate response functions are established for each sensor, such that each function provides for excursion between selected lower and upper pacing rates within the available range of sensor outputs corresponding therewith. Multiple rate response functions are provided to afford the necessary flexibility in providing alternative rate response settings to accommodate for various factors, such as: (a) group-based correlation drift wherein differences exist among a group of patients regarding their respective correlations between the sensor output and corresponding desired pacing rate; (b) individual-based correlation drift wherein the sensor output associated with the rate control parameter being measured does not remain constant over the life of the pacemaker for an individual patient primarily due to physiological changes of the patient over time, such as due to aging; and (c) non-physiological-based correlation drift wherein the sensor output associated with the rate control parameter being measured does not remain constant over the life of the pacemaker sensor primarily due to pacemaker performance changes, such as drift in sensor output.

The various rate response functions shown in FIGS. 2A and 2B are established in conjunction with programmable parameters provided by the patient's physician using an external programmer, in a manner which is generally similar to that described in two co-pending U.S. patent applications, namely, U.S. patent application Ser. No. 455,717, filed on Dec. 22, 1989, entitled "Method and Apparatus for Implementing Activity Sensing in a Pulse Generator" and U.S. patent application Ser. No. 549,568, filed on Jul. 6, 1990, entitled "Programming Non-Volatile Memory Through Hermetic Feedthrough", which are held by the same assignee as the present invention and which are incorporated herein by reference.

The target rates for each rate control parameter are determined as follows:

(Equation 2): ACTIVITY SENSOR ($S_1$):

$$\frac{(ACT. COUNT + D)}{C} * K = STR_{act}$$

(Equation 3): PRESSURE SENSOR ($S_2$):

$$\frac{(PRESS. AVG + B)}{A} * K = STR_{press}$$

In the above equations, $K=(32,768*60/328)$ and is a constant to convert clock cycle, time interval-based data to rate-based data (ppm), and A, B, C, and D constitute variables which are derived from programmed values provided by the external programmer during initialization.

Numerous programmable parameters, for example, will be established during initialization of pacemaker 100, which is described in the above incorporated '476 application. More specifically, variables A, B, C, and D are a function of the programmed Upper Rate (UR), Lower Rate (LR), and the respective rate response gain parameters (ACT.GAIN and PRESS.GAIN, for specific sensors, or RR in general), Resting Rate (REST.RATE), Resting (dP/dt) Pressure (REST.PRESS), and determine the shape desired for the various rate response curves illustrated, for example, in FIGS. 2A and 2B. Pacemaker 100 includes an arithmetic logic unit (ALU) capable of generating A, B, C and D values as a function of such programmed parameters, and for making the necessary calculations to generate the respective sensor target rates and controlling the pacemaker rate as a function thereof.

In the rate response graphs of FIGS. 2A and 2B, for example, a range of Target Rates extends between a Lower Rate (FIG. 2A) or a Resting Rate (FIG. 2B) of 40 ppm, and an Upper Rate of 175 ppm. Settings for rate response gain (ACT.GAIN and PRESS.GAIN for specific sensors, or RR in general) range from 1 to 10. It can be seen, for example, that the same magnitude of change in measured sensor output yields the greatest incremental change in target pacing rate under RR10, in contrast to the least incremental change in target pacing rate under RR1. The correlation thus defined between the sensor output and target pacing rate under these rate response curves is also often referred to as the "sensor gain function", wherein RR10 provides highest gain and RR1 provides lowest gain.

Each time the physician alters the selected values for UR, LR RR, REST.RATE and REST.PRESS via telemetry from the external programmer, these updated values are loaded into the program registers of pacemaker 100, such that new A, B, C and D values which are subsequently generated by the pacemaker 100 may be utilized by it in controlling the pacing rate as a function thereof. Regardless of which of the selected parameters has changed, the resulting function relating the Sensor Target Rate (STR) to sensor output, will take the basic form, extending from the Lower Rate (LR), or Resting Rate (REST.RATE) as appropriate, corresponding to a minimal sensor output, to the Upper Rate (UR) corresponding to an expected maximum sensor output, with a sensor output required to achieve UR decreasing as the rate response setting (RR) is increased.

The programmer also includes means for selection of acceleration and deceleration parameters which limit the rate of change in pacing rate on onset and cessation of activity, such as pacemaker 100 calculating the Sensor Pacing Rate (SPR) for each sensor as a function of its respective Sensor Target Rate (STR) and the contribution thereto based upon its respective acceleration and deceleration function. Typically, these acceleration and deceleration parameters are referred to in rate-responsive pacemakers as the attack or decay setting, respectively. These may be expressed as the time interval required for the pacemaker to change between the current pacing interval and 90% of the desired pacing interval, assuming that the physiologic stress level corresponding to the desired pacing rate remains constant, such as provided by ACT.ATTACK.TC, ACT.DECAY.TC, PRESS.ATTACK.TC and PRESS.DECAY.TC in the preferred embodiment. A more detailed description of the use of the above-described attack/decay settings in conjunction with pacemaker 100, including a modified decay feature which provides a pacing rate which decelerates at more than one decay time constant, is described in the above-incorporated '476 application.

Part VI. Achievement Criterion

Figure 3:
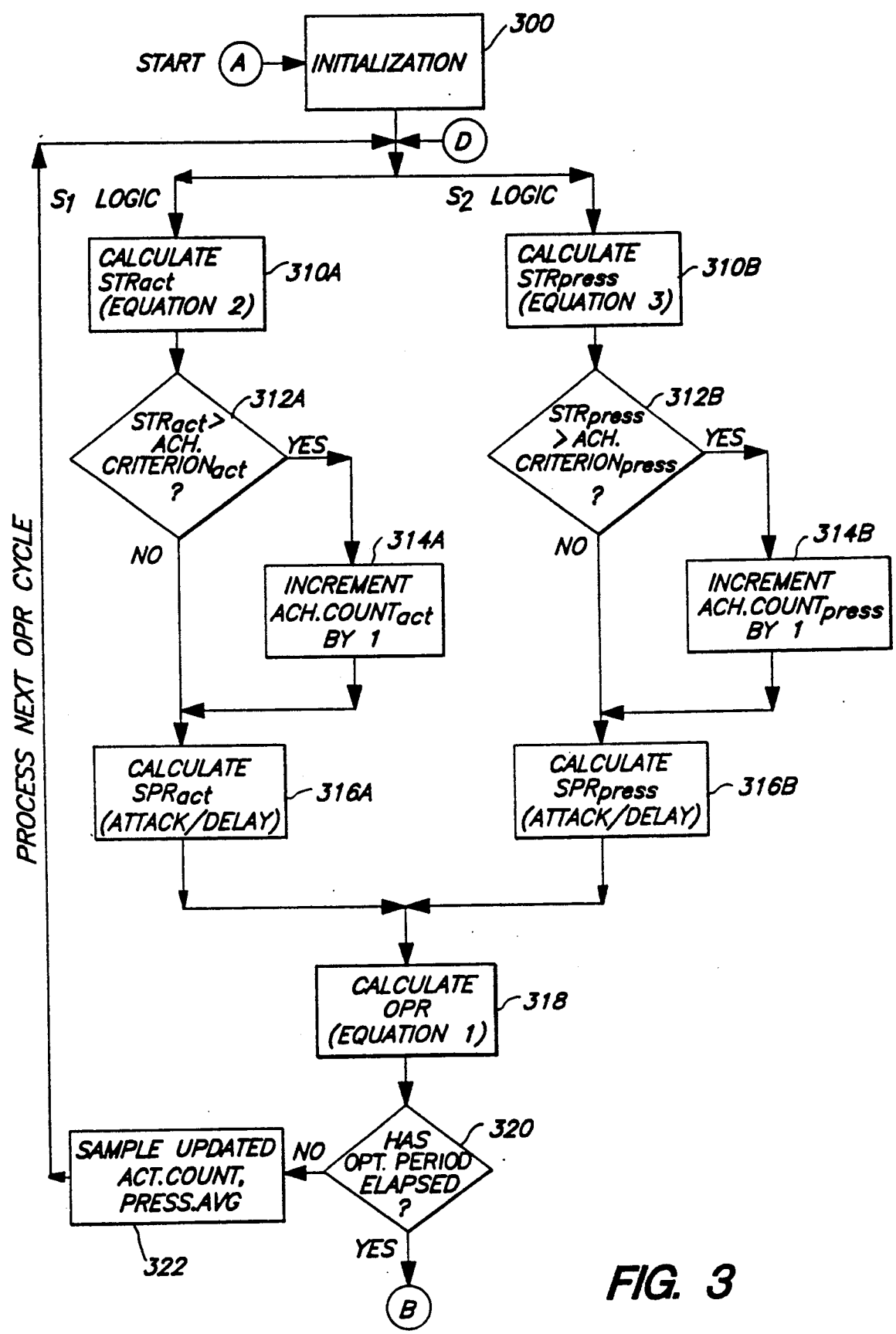
FIG. 3 is a simplified flowchart showing the basic function of software of the pacemaker of FIG. 1 for monitoring the attainment of achievement criterion for each of its sensors and for calculating an optimized pacing rate as a function thereof.

FIG. 3 is a simplified flowchart showing the basic function of software for monitoring the attainment of the Achievement Criterion by a pacemaker having at least two sensors of the type hereinabove described. It will be understood, however, that the software logic described in FIG. 3 is applicable to pacemakers having one, two or more sensors, for which an optimization of rate response as a function of an Achievement Criterion is desired.

Entering the flowchart at starting position A, block 300 corresponds to the initialization routine. At this time, the physician-selected parameters are established and programmed into storage registers in pacemaker 100 (FIG. 1) using conventional programming techniques, as hereinabove described. Various counters and flags associated with the various optimization procedures according to the present invention, which are hereinbelow described in connection with FIGS. 4 and 5, will also be initialized to the appropriate values at this time.

The remainder of FIG. 3 generally illustrates the software logic for a rate responsive pacemaker having two sensors, $S_1$ (sensing activity) and $S_2$ (sensing pressure), for purposes of monitoring the attainment of Achievement Criterion (ACH.CRITERION$_{act}$ and ACH.CRITERION$_{press}$) by each sensor's associated Sensor Target Rate (STR$_{act}$ and STR$_{press}$), throughout the duration of the Optimization Period (OPT.PERIOD). The left-hand side of FIG. 3 generally corresponds to the logic associated with $S_1$ by which its Achievement Count (ACH.COUNT$_{act}$) is incremented, and the right-side generally corresponds to the logic associated with $S_2$ by which its Achievement Count (ACH.COUNT$_{press}$) is incremented.

At blocks 310A and 310B, an STR associated with each sensor is calculated using Equations 2 and 3 hereinabove described in Part IV.

At blocks 312A and 312B, a determination is made as to whether the Achievement Criterion (ACH.CRITERION) has been met for each sensor. In particular, the STR associated with each sensor is compared with the ACH.CRITERION established for such sensor, to determine whether the STR has exceeded a threshold rate (Achievement Rate) for a predetermined time interval (Achievement Duration), and if so, the sensor's respective ACH.COUNT is incremented by 1 as shown at blocks 314A and 314B. In the preferred embodiment, since processing logistics of pacemaker 100 involve calculation of each sensor's STR in an alternating fashion, performing one STR calculation every two-second cycle, the Achievement Duration is set at 4 seconds to accommodate this operation. It will be understood, however, that these processing steps can be performed in parallel if desired, and the Achievement Duration can be shorter or longer as a function of such processing considerations.

At blocks 316A and 316B, an SPR associated with each sensor is calculated in a manner hereinabove described, based upon its most current STR and the contribution thereto required using the appropriate attack or decay function (ACT.ATTACK.TC, ACT.DECAY.TC, PRESS.ATTACK.TC and PRESS.DECAY.TC).

At block 318, assuming both sensors are enabled, the Optimized Pacing Rate (OPR) which pacemaker 100 will deliver is calculated based upon the current SPR values calculated for each sensor (SPR$_{act}$ and SPR$_{press}$) and the current Weighting Coefficient (COEFF) value for the present Optimization Period, using Equation 1 hereinabove described in Part III.

At block 320, pacemaker 100 determines whether the predetermined time interval associated with the Optimization Period (OPT.PERIOD) has elapsed. If not, pacemaker gathers new RCP-based data samples (i.e., updated ACT.COUNT and PRESS.AVG) shown at block 322, and resumes processing additional cycles in the manner described above. Once OPT.PERIOD has elapsed, pacemaker logic associated with optimization is initiated by exiting this flowchart at exit position B to commence optimization logic shown in FIGS. 4 and 5. In the preferred embodiment, OPT.PERIOD is selected at twenty-four hours, using crystal oscillator 138 which provides a real-time clock function. It will be understood that OPT.PERIOD can be set to be shorter or longer time intervals, if desired. A setting at 24 hours, however, is believed to provide a time interval which is an appropriate length to permit sufficient rate-response related data to be gathered between optimization procedures, while optimizing at a frequency which accommodates most patient's needs, including chronobiologic behaviors such as circadian rhythm. OPT.PERIOD can alternatively be set, for example, to multiples of twenty-four periods for accommodation of variations in patients' behavior, such as circadian rhythms or other factors.

Part VII. Optimization in General

Figure 4:
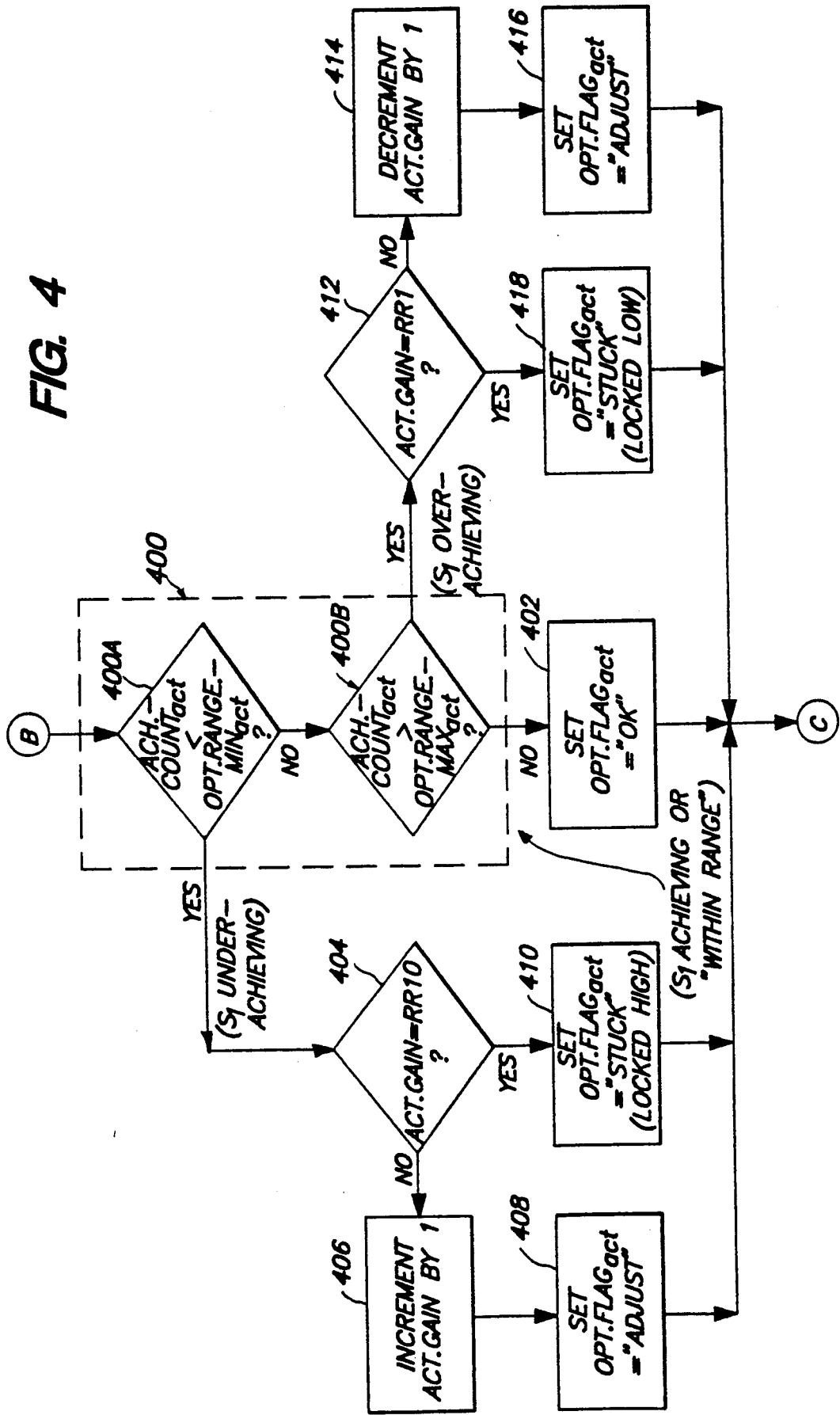
FIG. 4 is a simplified flowchart showing the basic function of software of the pacemaker of FIG. 1 for varying a sensor's rate response or gain as a function of its achievement criterion, such that the sensor's gain is automatically adjusted for purposes of deriving an optimized pacing rate.
Figure 5:
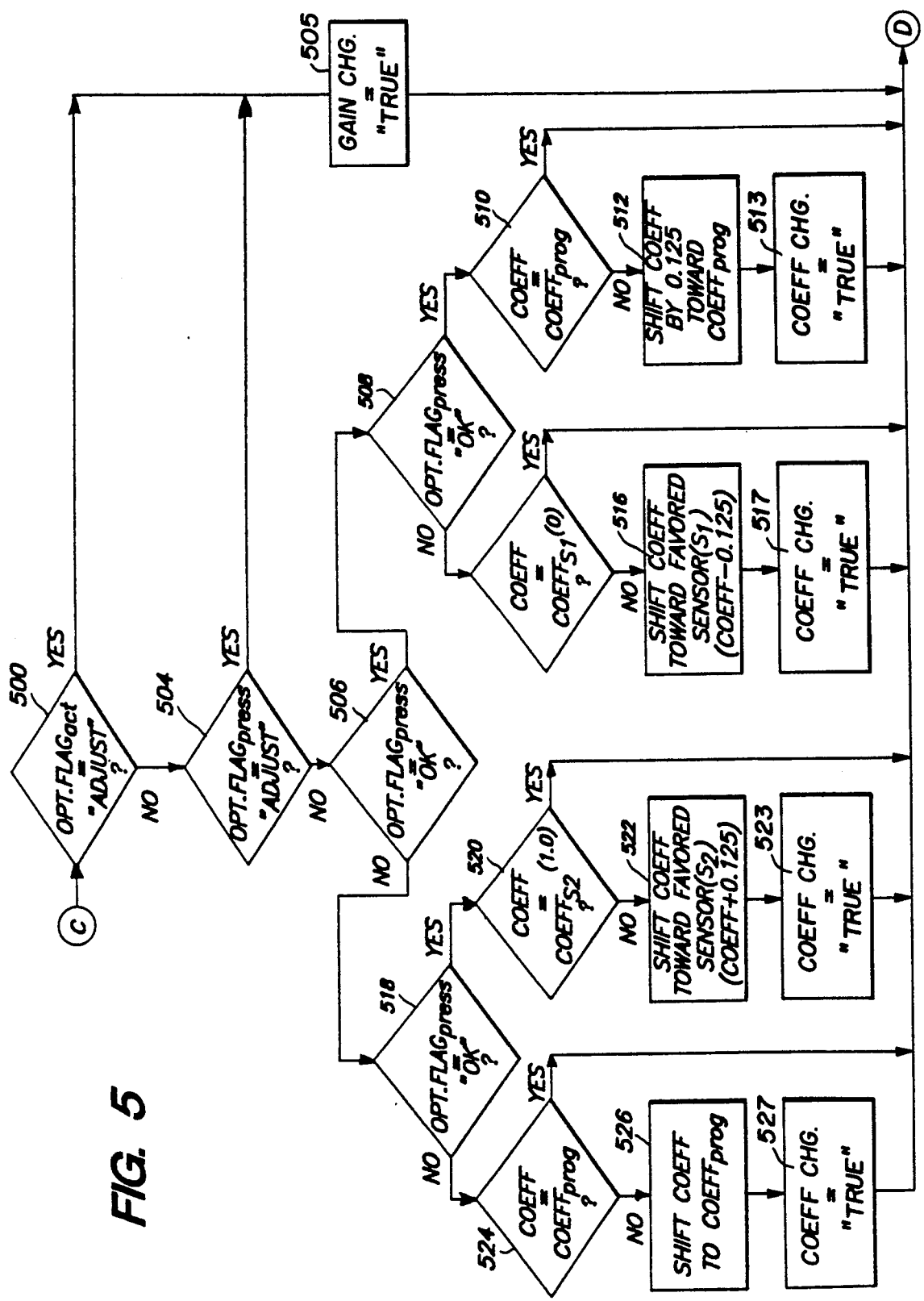
FIG. 5 is a simplified flowchart showing the basic function of software of the pacemaker of FIG. 1 for varying a sensor weighting coefficient as a function of each of the sensor's achievement criterion and sensor gain adjustment, such that the relative contribution or weighting given to each sensor's output and target pacing rate is automatically adjusted for purposes of deriving an optimized pacing rate.

FIGS. 4 and 5 are simplified flowcharts showing the basic function of software for performing optimization according to the present invention, for purposes of optimizing the rate of stimulus pulses (Optimized Pacing Rate or "OPR") being provided by pacemaker 100.

FIG. 4 relates to a sensor gain optimization procedure, useful in the context of a single or a multiple sensor-driven rate-responsive pacemaker, wherein a sensor's rate response or gain is varied as a function of its Achievement Criterion.

FIG. 5 relates to a sensor weighting optimization procedure, useful in the context of a multiple sensor-driven, rate-responsive pacemaker, wherein a sensor weighting coefficient (Weighting Coefficient or "COEFF") is varied as function of the rate response or gain adjustments which were made (i.e., varied from RR1 to RR10), if possible, for each sensor during the sensor gain optimization procedure. Thus, the Weighting Coefficient (COEFF) is varied as a function of the Achievement Criterion for each of the sensors, such that the proportion or weight of control given to each sensor's output is regulated appropriately for purposes of deriving an Optimized Pacing Rate for the patient.

The overall control logic of optimization according to the present invention, described in the simplified context of a two-sensor application, can be summarized as follows:

A. General Rules for Optimization (1) The Optimization Range (OPT.RANGE) for each sensor is defined by a minimum value (OPT.RANGE.MIN) and a maximum value (OPT.RANGE.MAX). At the end of each Optimization Period (OPT- .PERIOD), during each optimization cycle, the Achievement Count (ACH.COUNT) for each sensor is compared to its respective OPT.RANGE. Based upon such comparison, a sensor gain optimization (adjusting each sensor's rate response or gain (ACT.GAIN or PRESS.GAIN)) and/or a sensor weighting optimization (adjusting a Weighting Coefficient (COEFF)) are performed, if appropriate, by pacemaker 100 at the end of each OPT.PERIOD.

(2) A sensor gain is characterized as "underachieving" if its ACH.COUNT is less than the OPT.RANGE.MIN.

(3) A sensor gain is characterized as "overachieving" if its ACH.COUNT is greater than the OPT.RANGE.MAX.

(4) A sensor gain is characterized as "within range" or "achieving its criteria" if its ACH.COUNT is greater than or equal to its OPT.RANGE.MIN and less than or equal to its OPT.RANGE.MAX.

(5) A sensor gain is characterized as at "minimum gain" if it is set at its lowest available rate response setting (shown, for example, as RR1 in FIGS. 2A and 2B).

(6) A sensor gain is characterized as at "maximum gain" if it is set at its highest available rate response setting (shown, for example, as RR10 in FIGS. 2A and 2B).

(7) A sensor gain is characterized as "looked low" or "stuck" if, during the current optimization cycle, it is desired to decrease the sensor gain but it is already set at its lowest available rate response setting (e.g., RR1) due to an adjustment from a previous optimization cycle.

(8) A sensor gain is characterized as "locked high" or "stuck" if, during the current optimization cycle, it is desired to increase the sensor gain but it is already set at its highest available rate response setting (e.g., RR10) due to an adjustment from a previous optimization cycle.

(9) Adjustments to sensor gain (RR) are made in step increments or decrements of one setting at a time per optimization cycle (e.g., from RR3 to RR4).

(10) Adjustments to Weighting Coefficient (COEFF) are generally made in single step increments or decrements of 0.125 per optimization cycle based upon certain conditions encountered as specified below for the sensor weighting optimization procedure. A Programmed Coefficient Value ($COEFF_{PROG}$) is programmed during initialization with a desired value which will be used as an initial COEFF value for the first optimization procedure. Under certain conditions encountered during sensor weighting optimization as specified hereinbelow, the COEFF will be set to the $COEFF_{PROG}$, or be shifted toward the $COEFF_{PROG}$ in increments, in single steps.

(11) In the preferred embodiment having two sensors, for example, a single Weighting Coefficient (COEFF) is used according to Equation 1 hereinabove described and repeated below for convenience of the reader as follows:

$$OPR = [(1 - COEFF) * SPR_{act}] + (COEFF * SPR_{press}).$$

Thus, a simple means for adjusting the weight multiplier or "sensor coefficient" for each Sensor Pacing Rate (SPR) is provided, wherein the weight $SPR_{act}$ is given varies inversely with respect to the weight $SPR_{press}$ is given, as the COEFF is adjusted. Thus, for any COEFF value ranging from 0 to 1, the equivalent "sensor coefficient" for each SPR is as follows:

| SPR type | "sensor coefficient" value |
|---|---|
| $SPR_{act}$ | value = (1 - COEFF) |
| $SPR_{press}$ | value = COEFF |

Therefore, making an adjustment in the COEFF such that a particular selected or favored sensor's SPR will be given greater weight or emphasis than the other sensor's SPR (i.e., the selected sensor's "sensor coefficient" will be increased and the other sensor's "sensor coefficient" will be decreased) is characterized as "shifting the COEFF toward the favored sensor". In the preferred embodiment, for example, "shifting the COEFF toward the favored sensor" requires the following adjustment in the COEFF:

| Favored Sensor (SPR type) | COEFF Adjustment |
|---|---|
| $S_1$ ($SPR_{act}$) | Decrement COEFF |
| $S_2$ ($SPR_{press}$) | Increment COEFF. |

Consequently, a COEFF value of 0 will most heavily favor the weighting for $S_1$ ($COEFF_{S1}$), and a COEFF value of 1.0 will most heavily favor the weighting for $S_2$ ($COEFF_{S2}$).

(12) An Optimization Flag (OPT.FLAG) corresponding to each sensor (e.g., $OPT.FLAG_{act}$ and $OPT.FLAG_{press}$) is used to provide an indication of optimization activity taken with respect to sensor gain optimization for each sensor. OPT.FLAG can be set to three different values (e.g., 1, 2 or 3) which correspond to three conditions ("OK", "ADJUSTED" or "STUCK") identifying the type of optimization activity taken:

| Condition | Optimization Activity |
|---|---|
| "OK" | Gain adjustment not needed and not made (snce ACT.COUNT is within OPT.RANGE). |
| "ADJUSTED" | Gain was adjusted by increment or decrement (required since ACT.COUNT is outside of OPT.RANGE). |
| "STUCK" | Gain adjustment was needed but could not be made (although ACT.COUNT was outside of OPT.RANGE, sensor gain was locked high or locked low). |

B. Rules for Sensor Gain Optimization (1) If a sensor is within range, its sensor gain will not be adjusted.

(2) If a sensor is overachieving and its gain is not at minimum gain, its gain will be decreased one setting.

(3) If a sensor is underachieving and its gain is not at maximum gain, its gain will be increased one setting.

(4) Gain for both sensors can be changed each optimization cycle if conditions B(2) or B(3) exist.

(5) If a sensor is overachieving and its sensor gain is already set at minimum (i.e., stuck in a locked low condition), then its sensor gain cannot be decreased further, and no sensor gain adjustment will be made.

(6) If a sensor is underachieving and its gain is already set at maximum gain (i.e., stuck in a locked high condition), then its sensor gain cannot be increased further, and no sensor gain adjustment will be made.

C. Rules for Sensor Weighting Optimization (1) If a sensor's gain is adjusted in an optimization cycle, no adjustment in that sensor's "sensor coefficient" will be made during that optimization cycle (i.e., no adjustment to the COEFF value will be made during that cycle). Thus, in the preferred embodiment, when only one sensor's gain is adjusted, regardless of the gain optimization activity for the other sensor, no adjustment in weighting will be performed during that cycle.

(2) If both sensor gains are adjusted in an optimization cycle, no adjustment in weighting will be made during that optimization cycle (i.e., no adjustment to the COEFF value will be made during that cycle).

(3) If both sensors are within range (i.e., achieving their criteria), regardless of their gain settings, the weighting coefficient is adjusted one setting from its current COEFF value (i.e., a single step increment or decrement of 0.125) toward the Programmed Coefficient Value (COEFF$_{PROG}$).

(4) If both sensors are underachieving and both sensor gains are already set at maximum gain (i.e., both sensor gains are stuck in a locked high condition), the COEFF is shifted from its current value to the COEFF$_{PROG}$ in a single adjustment.

(5) If both sensors are overachieving and both sensor gains are already set at minimum gain (i.e., both sensor gains are stuck in a locked low condition), the COEFF is shifted from its current value to the COEFF$_{PROG}$ in a single adjustment.

(6) If one of the sensors is overachieving and its sensor gain is already set at minimum gain (i.e., its sensor gain is stuck in a locked low condition), and the other sensor is underachieving and its sensor gain is already set at maximum gain (i.e., its sensor gain is stuck in a locked high condition), the COEFF is shifted from its current value to the COEFF$_{PROG}$ in a single adjustment.

(7) If one of the sensors is underachieving and its sensor gain is set at maximum (i.e., its sensor gain is stuck in a locked high condition) and the other sensor is within range, then the sensor which is within range is be characterized as the "favored sensor" and the other sensor whose sensor gain is stuck is characterized as the "stuck sensor". In this situation, the COEFF is adjusted one setting from its current COEFF value (i.e., a single step increment or decrement of 0.125), by "shifting toward the favored sensor" (i.e., the favored sensor's SPR will be given greater weight or emphasis than the stuck sensor's SPR).

(8) If one of the sensors is overachieving and its sensor gain is set at minimum (i.e., its sensor gain is stuck in a locked low condition) and the other sensor is within range, then the sensor which is within range is be characterized as the "favored sensor" and the other sensor whose sensor gain is stuck is characterized as the "stuck sensor". In this situation, the COEFF is adjusted one setting from its current COEFF value (i.e., a single step increment or decrement of 0.125), by "shifting toward the favored sensor" (i.e., the favored sensor's SPR will be given greater weight or emphasis than the stuck sensor's SPR).

Part VIII. Sensor Gain Optimization Procedure

FIG. 4 illustrates the basic function of software for performing optimization of sensor gain, according to the present invention. For ease of explanation, sensor gain optimization logic is shown for one sensor only, using the activity (first) sensor $S_1$ for this example. It will be understood, however, that the software logic described in FIG. 4 is applicable to pacemakers having one, two, or more sensors, for which an optimization of sensor rate response or gain as a function of an Achievement Criterion is desired, and the logic is essentially identical for each sensor gain being optimized (e.g., for optimizing PRESS.GAIN for the second sensor $S_2$).

Entering the flowchart at starting position B, a determination is made at composite block, shown by dashed lines at 400, as to whether the sensor's Achievement Count (ACH.COUNT$_{act}$) is "within range" of its Optimization Range (OPT.RANGE$_{act}$), namely, whether OPT.RANGE.MIN$_{act}$ < ACH.COUNT.$_{act}$ < OPT.RANGE.MAX$_{act}$. A determination that ACH.COUNT$_{act}$ was "within range" for the twenty-four hour Optimization Period (OPT.PERIOD) which has just elapsed is indicative that the sensor's gain (ACT.GAIN) or rate response setting (RR) was appropriate for the patient's needs, and no sensor gain adjustment is necessary for gain optimization.

A determination is first made at block 400A as to whether the activity sensor was underachieving, namely, whether its Achievement Count is below its Optimization Range (i.e., whether ACH.COUNT$_{act}$ < OPT.RANGE.MIN$_{act}$). A decision of NO at block 400A results if the sensor was not underachieving (i.e., ACH.COUNT$_{act}$ >, or = OPT.RANGE.MIN$_{act}$). Consequently, a determination is then made at block 400B as to whether the activity was overachieving, namely, whether its Achievement Count is above its Optimization Range (i.e., whether ACH.COUNT$_{act}$ > OPT.RANGE.MAX$_{act}$). A decision of NO at block 400B results if the sensor was not overachieving (i.e., ACH.COUNT$_{act}$ <, or = OPT.RANGE.MAX$_{act}$). Under these conditions, no sensor gain adjustment is required, and the Optimization Flag (OPT.FLAG$_{act}$) is set at block 402 to "OK" status, followed by exiting this flowchart at exit position C to commence the sensor weighting optimization logic shown in FIG. 5.

A determination, however, at composite block 400 that the sensor's Achievement Count (ACH.COUNT$_{act}$) is not "within range" of its Optimization Range (OPT.RANGE$_{act}$) being used for the Optimization Period (OPT.PERIOD) which has just elapsed (i.e., the sensor was either underachieving or overachieving), will cause pacemaker 100 to perform the remainder of optimization logic shown in FIG. 4. A determination that the Achievement Count is not "within range" indicates that the sensor gain was not set to optimally meet the needs of the patient over the previous Optimization Period which has just elapsed (i.e., ACT.GAIN should be incremented or decremented for the next Optimization Period, since sensor $S_1$ was either overachieving or underachieving its Achievement Criterion). The objective, therefore, of this optimization logic will be to cause, if possible, an adjustment to be made to the sensor gain (increment or decrement). The gain adjustment will be made by pacemaker 100 in such a manner that the sensor's Achievement Count developed during the next Optimization Period will be more likely to fall "within range" of its Optimization Range. Consequently, the activity-driven, rate response behavior of pacemaker 100 will be optimized as a function of the Achievement Criterion for the activity sensor.

Returning to composite block 400, a decision of YES results at block 400A if sensor $S_1$ was underachieving (i.e., ACH.COUNT$_{act}$ < OPT.RANGE.MIN$_{act}$). To provide a desired gain optimization in response to such detected underachievement, a determination is then made at block 404 as to whether the sensor gain (ACT GAIN) is "stuck", or alternatively, whether it can be increased. A decision of NO results at block 404 if the current gain setting is not already set at its highest available sensor gain or rate response setting (i.e., NO if ACT.GAIN is not stuck in locked high condition which corresponds to the "maximum gain" of RR10 as shown in FIG. 2A in the preferred embodiment). Consequently, the sensor gain will be incremented one setting (e.g., from RR5 to RR6) at block 406 by means of pacemaker 100 performing calculations which modify variables A, B, C and D to derive an adjusted rate response function. The Optimization Flag (OPT.GAIN$_{act}$) is set at block 408 to "ADJUSTED" status, followed by exiting this flowchart at exit position C to commence the sensor weighting optimization logic shown in FIG. 5.

Conversely, a decision of YES results at block 404 if the current gain setting is already set at its highest available sensor gain or rate response setting (i.e., YES if ACT.GAIN=RR10). Therefore, ACT.GAIN is locked high and no further increase in sensor gain can be performed. Consequently, the Optimization Flag (OPT.GAIN$_{act}$) is set at block 410 to "STUCK" status, followed by exiting this flowchart at exit position C to commence the sensor weighting optimization logic shown in FIG. 5.

Returning again to composite block 400, a decision of YES results at block 400B if sensor S$_1$ was overachieving (i.e., ACH.COUNT$_{act}$>OPT.RANGE.MAX$_{act}$). To provide a desired gain optimization in response to such detected overachievement, a determination is then made at block 412 as to whether the sensor gain (ACT.GAIN) is "stuck" or alternatively, whether it can be decreased. A decision of NO results at block 412 if the current gain setting is not already set at its lowest available sensor gain or rate response setting (i.e., NO if ACT.GAIN is not stuck in locked low condition which corresponds to the "minimum gain" of RR1 as shown in FIG. 2A in the preferred embodiment). Consequently, the sensor gain will be decremented one setting (e.g., from RR5 to RR4) at block 414 by means of pacemaker 100 performing calculations which modify variables A, B, C and D to derive an adjusted rate response function. The Optimization Flag (OPT.GAIN$_{act}$) is set at block 416 to "ADJUSTED" status, followed by exiting this flowchart at exit position C to commence the sensor weighting optimization logic shown in FIG. 5.

Conversely, a decision of YES results at block 412 if the current gain setting is already set at its lowest available sensor gain or rate response setting (i.e., YES if ACT.GAIN=RR1). Therefore, ACT.GAIN is locked low and no further decrease in sensor gain can be performed. Consequently, the Optimization Flag (OPT.GAIN$_{act}$) is set at block 418 to "STUCK" status, followed by exiting this flowchart at exit position C to commence the sensor weighting optimization logic shown in FIG. 5.

It will be understood that the same sensor gain optimization logic shown in FIG. 4 will also be performed for the second sensor S$_2$, commencing at starting position B and concluding at exit position C, to provide the appropriate adjustment, if possible, to the pressure sensor's gain (PRESS.GAIN).

It will also be understood by those skilled in the art that the particular technique by which the foregoing sensor gain is adjusted for optimization is not critical, and that several alternatives are available. Some alternatives which are regarded as functional equivalents to the specific type of sensor gain adjustment described above can include, for example: (1) selectively adjusting the threshold for sensor output (e.g., ACT.THRESH); (2) selectively adjusting the sensor's amplification of the raw sensor signal; or (3) selectively adjusting the sensor output value mathematically by means of a range of output multiplier values.

Part IX. Sensor Weighting Optimization Procedure

FIG. 5 illustrates the basic function of software for performing optimization of sensor Weighting Coefficient (COEFF), according to the present invention. At the end of each Optimization Period, following the sensor gain optimization procedure described in FIG. 4, the sensor weighting optimization procedure will be performed. The objective of this optimization logic will be to cause, if possible, the Weighting Coefficient to be varied as function of the rate response or gain adjustments which were made, if possible, for each sensor during the sensor gain optimization procedure. Thus, the Weighting Coefficient (COEFF) is varied as a function of the Achievement Criterion for each of the sensors, such that the proportion or weight of control given to each sensor's output is regulated appropriately for purposes of deriving an Optimized Pacing Rate for the patient.

Upon entering the flowchart at starting position C, the Optimization Flag for activity sensor S$_1$ (OPT.FLAG$_{act}$) and the Optimization Flag for pressure sensor S$_2$ (OPT.FLAG$_{press}$) will have been set to their respective values which correspond to the optimization activity performed during the sensor gain optimization cycle described in FIG. 4 (e.g., OPT FLAG="OK" "ADJUSTED" or "STUCK"). Adjustments made in the sensor weighting optimization procedure will be made based upon the respective values for each of these Optimization Flags, according to the logic rules hereinabove described in Part VII.

A determination is made at block 500 as to whether the gain for S$_1$ was adjusted. A decision of YES at block 500 results if the first sensor is rate response (ACT.GAIN) was adjusted (i.e., Yes if OPT.FLAG$_{act}$="ADJUSTED"). At this point, therefore, OPT FLAG$_{act}$ ="ADJUSTED" and OPT.FLAG$_{press}$ corresponds to either "OK", "ADJUSTED" or "STUCK". Under this condition, no adjustment to the Weighting Coefficient is necessary.

A decision of NO at block 500 results if the first sensor's rate response (ACT.GAIN) was not adjusted during the sensor gain optimization procedure. At this point, therefore, OPT.FLAG$_{act}$ corresponds to either "OK" or "STUCK" and OPT FLAG$_{press}$ corresponds to either "OK" "ADJUSTED" or "STUCK".

A determination is then made at block 504 as to whether the gain for S$_2$ was adjusted. A decision of YES at block 504 results if the second sensor Is rate response (PRESS. GAIN) was adjusted ( i.e., Yes if OPT.FLAG$_{press}$="ADJUSTED"). At this point, therefore, OPT.FLAG$_{act}$ corresponds to either "OK" or "STUCK" and OPT FLAG$_{press}$="ADJUSTED". Under this condition, no adjustment to the Weighting Coefficient is necessary.

A decision of NO at block 504 results if the second sensor's rate response (PRESS.GAIN) was not adjusted during the sensor gain optimization procedure. At this point, therefore, OPT.FLAG$_{act}$ corresponds to either "OK" or "STUCK" and OPT.FLAG$_{press}$ corresponds to either "OK" or "STUCK".

A determination is then made at block 506 as to which of the two remaining situations account for the absence of a gain adjustment for S$_1$, namely, whether OPT.FLAG$_{act}$ corresponds to "OK" or "STUCK". The specific test used is whether OPT.FLAG$_{act}$ corresponds to "OK".

A decision of YES at block 506 results if the non-adjustment was due to the fact that S$_1$ was achieving its Achievement Criterion, namely, that its ACH.COUNT$_{act}$ was "within range" of its OPT.RANGE$_{act}$ (i.e., YES if OPT.FLAG$_{act}$ corresponds to "OK"). At this point, therefore, OPT.FLAG$_{act}$ corresponds to "OK", and OPT.FLAG$_{press}$ corresponds to either "OK" or "STUCK".

Following a decision of YES at block 506, a determination is then made at block 508 as to which of the two remaining situations account for the absence of a gain adjustment for S2, namely, whether OPT.FLAG$_{press}$ corresponds to "OK" or "STUCK". The specific test used is whether OPT.FLAG$_{press}$ corresponds to "OK".

Figure 15:
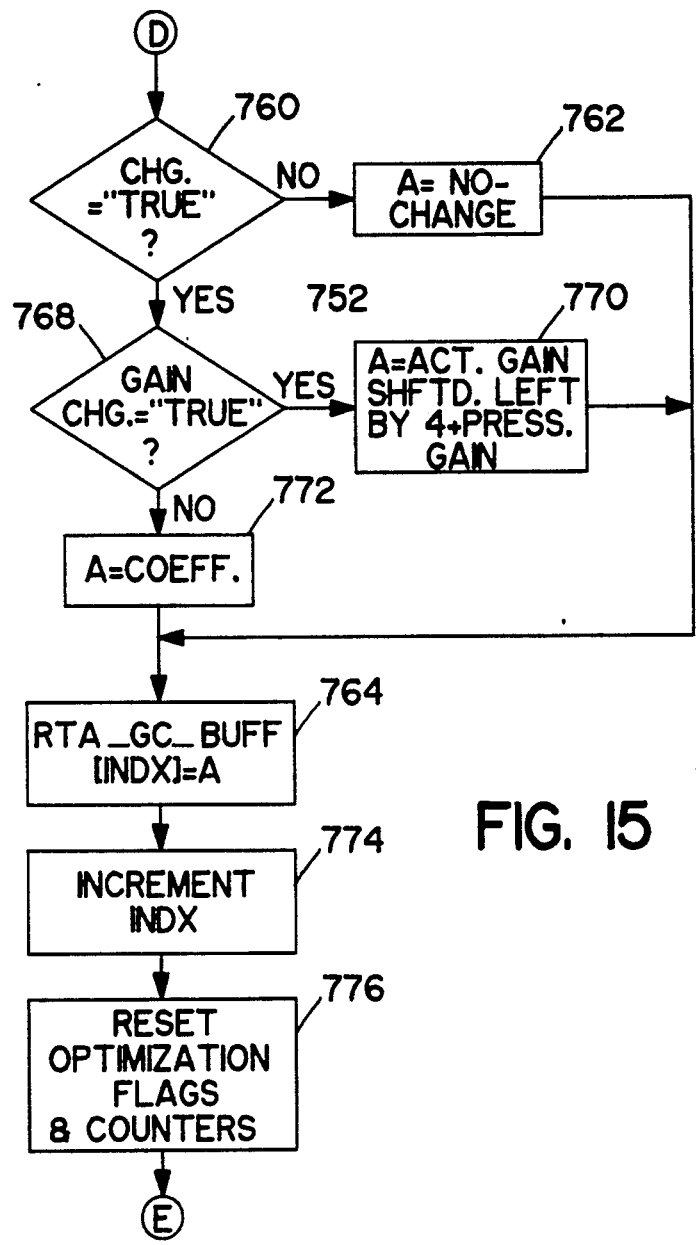
FIG. 15 is a simplified flow chart of the algorithm for storing, on a daily basis, a number of ACT.GAIN, PRESS.GAIN and COEFF values in memory buffer stages illustrated in FIG. 9 (Maps 3-4)

A decision of YES at block 508 results if the non-adjustment was due to the fact that S$_2$ was achieving its Achievement Criterion, namely, that its ACH.COUNT$_{press}$ was "within range" of its OPT.RANGE$_{press}$ (i.e., YES if OPT.FLAG$_{press}$ corresponds to "OK"). At this point, therefore, OPT.FLAG$_{act}$ and OPT.FLAG$_{press}$ both correspond to "OK". Under this condition, it is desirable to adjust the current COEFF value toward the COEFF$_{PROG}$ in a single step increment or decrement of 0.125. A determination is first made at block 510 as to whether the Weighting Coefficient (COEFF) is already set at its Programmed Coefficient Value (COEFF$_{PROG}$). If a decision of YES at block 510 results, no adjustment to COEFF is necessary and this flowchart is exited at position D to commence storing optimization status and data as shown in FIG. 15. A decision of NO at block 510 requires the current COEFF value be adjusted at block 512 toward the COEFF$_{PROG}$ in a single step increment or decrement of 0.125.

Returning again to block 508, a decision of NO results at block 508 if the non-adjustment was due to the fact that S$_2$ was failing to achieve its Achievement Criterion and its desired gain adjustment could not be made because it was stuck in locked high condition (i.e., RR10 while underachieving) or it was stuck in locked low condition (i.e., RR1 while overachieving) (i.e., NO if OPT.FLAG$_{press}$ corresponds to "STUCK"). At this point, therefore, OPT.FLAG$_{act}$ corresponds to "OK", and OPT.FLAG$_{press}$corresponds to "STUCK". In this situation, S$_1$ is considered the "favored sensor" and S$_2$ is considered the "stuck sensor". Under this condition, it is desirable to shift the COEFF toward the favored sensor, such that the Sensor Pacing Rate for the favored sensor (SPR$_{act}$) is given greater weight or emphasis than that of the stuck sensor (SPR$_{press}$) for purposes of deriving the Optimized Pacing Rate (OPR) according to Equation 1 hereinabove set forth in Part III. This is accomplished by shifting from the current COEFF value toward a COEFF value which will most heavily favor the weighting for S$_1$. In the preferred embodiment, the limit to which COEFF can be shifted to most heavily weight SPR$_{act}$ is a COEFF setting of 0 (such limit referred to as COEFF$_{S1}$). A determination is first made at block 514, therefore, as to whether the COEFF is already set at COEFF$_{S1}$. If a decision of YES at block 514 results, no adjustment to COEFF is necessary and this flowchart is exited at position D to commence storing optimization status and data as shown in FIG. 15. If a decision of NO at block 514 results, the current COEFF value is adjusted at block 516 toward the favored sensor (i.e., adjust the COEFF value toward its limit of COEFF$_{S1}$) in a single step decrement of 0.125.

Returning again to block 506, a decision of NO at block 506 results if the non-adjustment was due to the fact that S$_1$ was failing to achieve its Achievement Criterion and its desired gain adjustment could not be made because it was stuck in locked high condition (i.e., RR10 while underachieving) or it was stuck in locked low condition (i.e., RR1 while overachieving) (i.e., NO if OPT.FLAG$_{act}$ corresponds to "STUCK"). At this point, therefore, OPT FLAG$_{act}$ corresponds to "STUCK" and OPT FLAG$_{press}$ corresponds to either "OK" or "STUCK".

Following a decision of NO at block 506, a determination is then made at block 518 as to which of the two remaining situations account for the absence of a gain adjustment for S$_2$, namely, whether OPT.FLAG$_{press}$ corresponds to "OK". or "STUCK". The specific test used is whether OPT.FLAG$_{press}$ corresponds to "OK".

A decision of YES at block 518 results if the non-adjustment was due to the fact that S$_2$ was achieving its Achievement Criterion, namely, that its ACH.COUNT$_{press}$ was "within range" of its OPT.RANGE$_{press}$ (i.e., YES if OPT.FLAG$_{press}$ corresponds to "OK"). At this point, therefore, OPT.FLAG$_{act}$ corresponds to "STUCK" and OPT.FLAG$_{press}$ corresponds to "OK". In this situation, S$_2$ is considered the "favored sensor" and S$_1$ is considered the "stuck sensor". Under this condition, it is desirable to shift the COEFF toward the favored sensor, such that the Sensor Pacing Rate for the favored sensor (SPR$_{press}$) is given greater weight or emphasis than that of the stuck sensor (SPR$_{act}$) for purposes of deriving the Optimized Pacing Rate (OPR) according to Equation 1 hereinabove set forth in Part III. This is accomplished by shifting from the current COEFF value toward a COEFF value which will most heavily favor the weighting for S$_2$. In the preferred embodiment, the limit to which COEFF can be shifted to most heavily weight SPR$_{press}$ is a COEFF setting of 1.0 (such limit referred to as COEFF$_{S2}$). A determination is first made at block 520, therefore, as to whether the COEFF is already set at COEFF$_{S2}$. If a decision of YES at block 520 results, no adjustment to COEFF is necessary. If a decision of NO at block 520 results, the current COEFF value is adjusted at block 522 toward the favored sensor (i.e., adjust the COEFF value toward its limit of COEFF$_{S1}$) in a single step increment of 0.125, followed by exiting at D to commence storing Optimization status and data as shown in FIG. 15.

Returning again to block 518, a decision of NO at block 518 results if the non-adjustment was due to the fact that S$_2$ was failing to meet it Achievement Criterion and its desired gain adjustment could not be made because it was stuck in locked high condition (i.e., RR10 while underachieving) or it was stuck in locked low condition (i.e., RR1 while overachieving) (i.e., NO if OPT.FLAG$_{press}$ corresponds to "STUCK"). At this point, therefore, OPT.FLAG$_{act}$ and OPT.FLAG$_{press}$ both correspond to "STUCK". Under this condition, it is desirable to adjust the COEFF from its current value to the COEFF$_{PROG}$ in a single adjustment. For example, if COEFF$_{PROG}$ is programmed at 0.500 and the current value of COEFF is 0.750, then a single adjustment decrementing COEFF by 0.250 to the programmed value of 0.500 would be made. A determination is first made at block 524 as to whether the current value of the Weighting Coefficient (COEFF) is already set at its Programmed Coefficient Value (COEFF$_{PROG}$). If a decision of YES at block 524 results, no adjustment to COEFF is necessary. Therefore, appropriate resetting functions at block 502 are performed, followed by exiting this flowchart at exit position D to commence another Optimization Period. A decision of NO at block 524 requires the current COEFF value be adjusted at block 526 from it current COEFF value to the COEFF$_{PROG}$ in a single adjustment, followed by exiting at D to commence storing optimization status and data as shown in FIG. 15.

Figure 17:
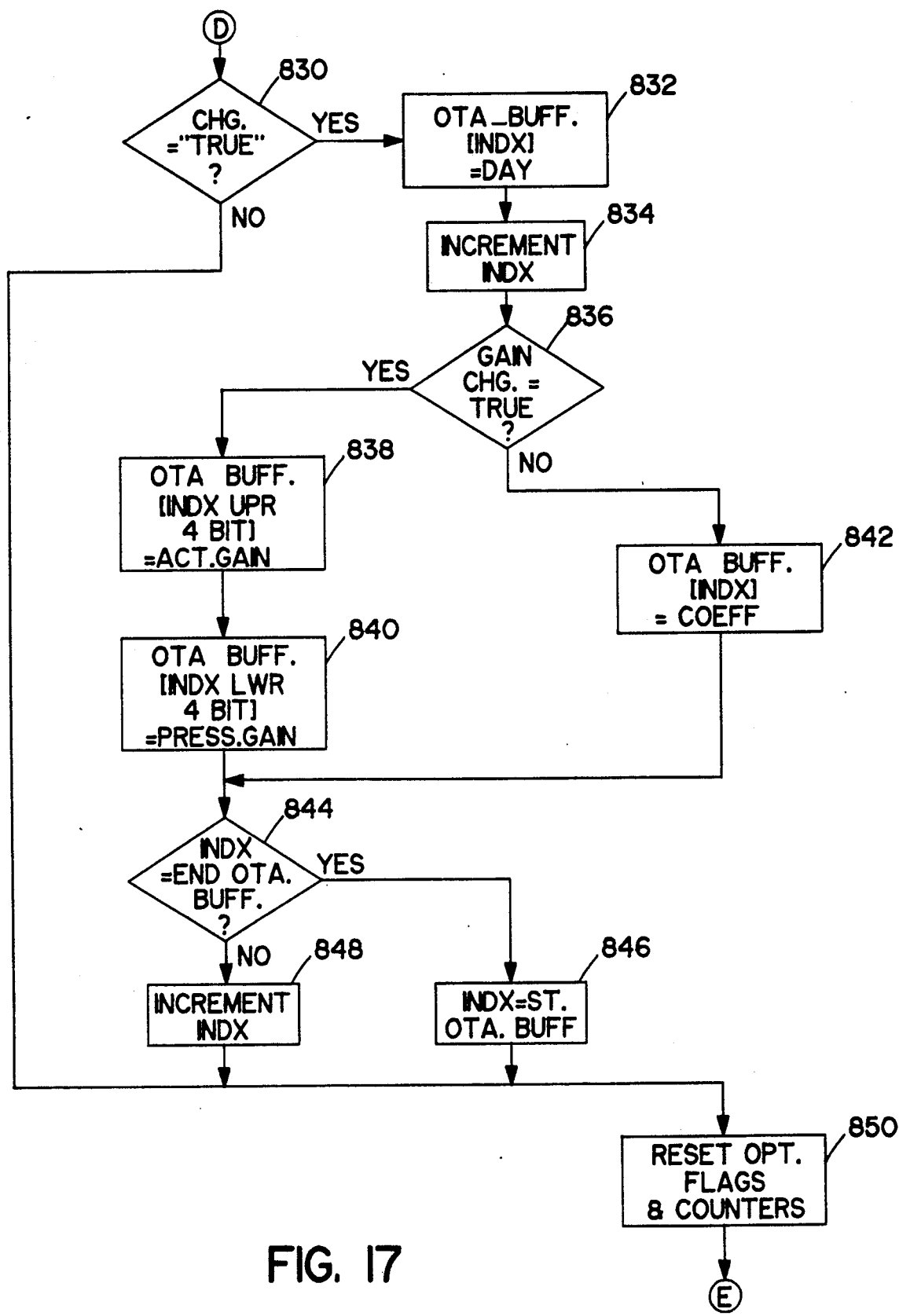
FIG. 17 is a simplified flow chart of the optimization trend analysis diagnostic algorithm which stores the last 52 ACT.GAIN, PRESS.GAIN and COEFF values, as well as the day the changes occurred, in memory buffer stages illustrated in FIG. 9 (Map 4)

If the gain for $S_1$ and/or $S_2$ is adjusted, a GAIN CHG. = "TRUE" register is flagged in block 505. Similarly, if the coefficient is adjusted in any of the possible ways illustrated in FIG. 5, a corresponding COEFF.CHG = "TRUE" is flagged in one of the blocks 527, 523, 517 or 513. These flagged events are employed in the OPTIMIZATION TREND ANALYSIS (OTA) of FIG. 17 and in conjunction with FIG. 15 in providing uplink measured value telemetry of the. logged and sensor current/given and weighting coefficient. As stated earlier, the optimization takes place on a daily basis and thus logging of these values in memory takes place on a daily basis if changes have been made.

Part X. Automatic Capture and Loss of Capture Detection

The energy of a pacing pulse may be sufficient to exceed the stimulation threshold of the heart (and "capture" the heart by causing a contraction to follow) or not, depending on a number of well known factors. A "loss of capture" or LOC is said to occur when the pacing pulse fails to elicit a contraction or capture the heart. The pacemaker of FIG. 1 can be permanently enabled to automatically adjust the ventricular output stimulus amplitude or pulse width to maintain capture. This algorithm is used to control the pulse generator's output energy to allow aggressive programming of output parameters to optimize longevity while assuring that a user programmable safety margin is maintained. The operating parameter Value is determined by an algorithm which considers detection of mechanical systole within a 170 millisecond-wide pressure window beginning 30 msec following the delivery of a stimulus to be evidence of capture. The algorithm protects against positive feedback due to exit block when pacing near the programmed upper rate. This function is independent of rate variability but is only allowed in the VVI, VVT, and VVIR modes. This function is available only when the pressure sensor $S_2$ lead is connected.

Figure 6:
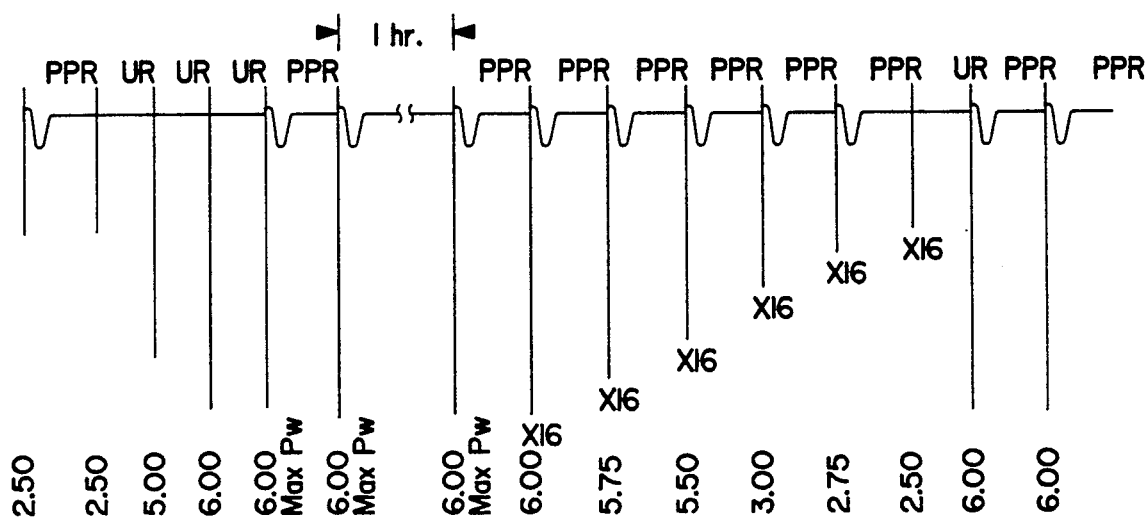
FIG. 6 is an illustration of the auto capture, loss of capture and recovery sequence of one of the modes of operation of the pacemaker of FIG. 1.

In reference to FIG. 6, upon detection of LOC, the selected pulse "METRIC" (pulse width or amplitude) is set to programmed safety margin or set to maximum whichever is less. A stimulus is delivered at the programmed Upper Rate (UR) period. If LOC continues, the second stimulus is delivered (at the UR period) at its maximum setting and, if already set at its maximum, the unselected "NON-METRIC" is set to its maximum value. If LOC continues and both METRICs are not at their maximum, the third stimulus is delivered at the UR with both pulse width and amplitude at their maximum settings.

Pacing at the level that capture has resumed continues for one hour before a threshold seeking sequence is enabled. The unselected pulse METRIC is returned to its programmed value while the selected metric is decremented in discrete steps (16 stimuli at each step, PW in 30 sec steps and PA in 0.25 V steps) until the programmed value is reached. If capture is lost during the recovery sequence, the LOC algorithm is re-initiated (to previous paragraph). Intrinsic sensed events suspend the loss of capture response and the tracking function with all values intact until resumption of pacing. FIG. 6 illustrates both the LOC response and the recovery from LOC is described above.

This algorithm is suspended and reset upon reed switch closure and resumes upon reed switch opening. However, the response to a loss of capture (the increase in pulse METRICs to regain capture) will complete upon reed switch closure. Valid sensed events during the response to a loss of capture will stop and reset the algorithm as if capture had been recovered.

A programmable (25-75%, in 12.5% steps) threshold of a stored average pulse pressure value (a continuous running average of 16 pulse pressure values) will be used to determine successful capture due to a stimulating pulse. A fixed, lowest threshold of 4 mmHg will be allowed to prevent false detection during capture detection. A running average of the last 16 paced and sensed events is used to generate the running average. All events' (paced and sensed) pulse pressure amplitudes are included in the average even if below the programmed threshold (but must be above the 4 mmHg fixed lower threshold).

Figure 7:
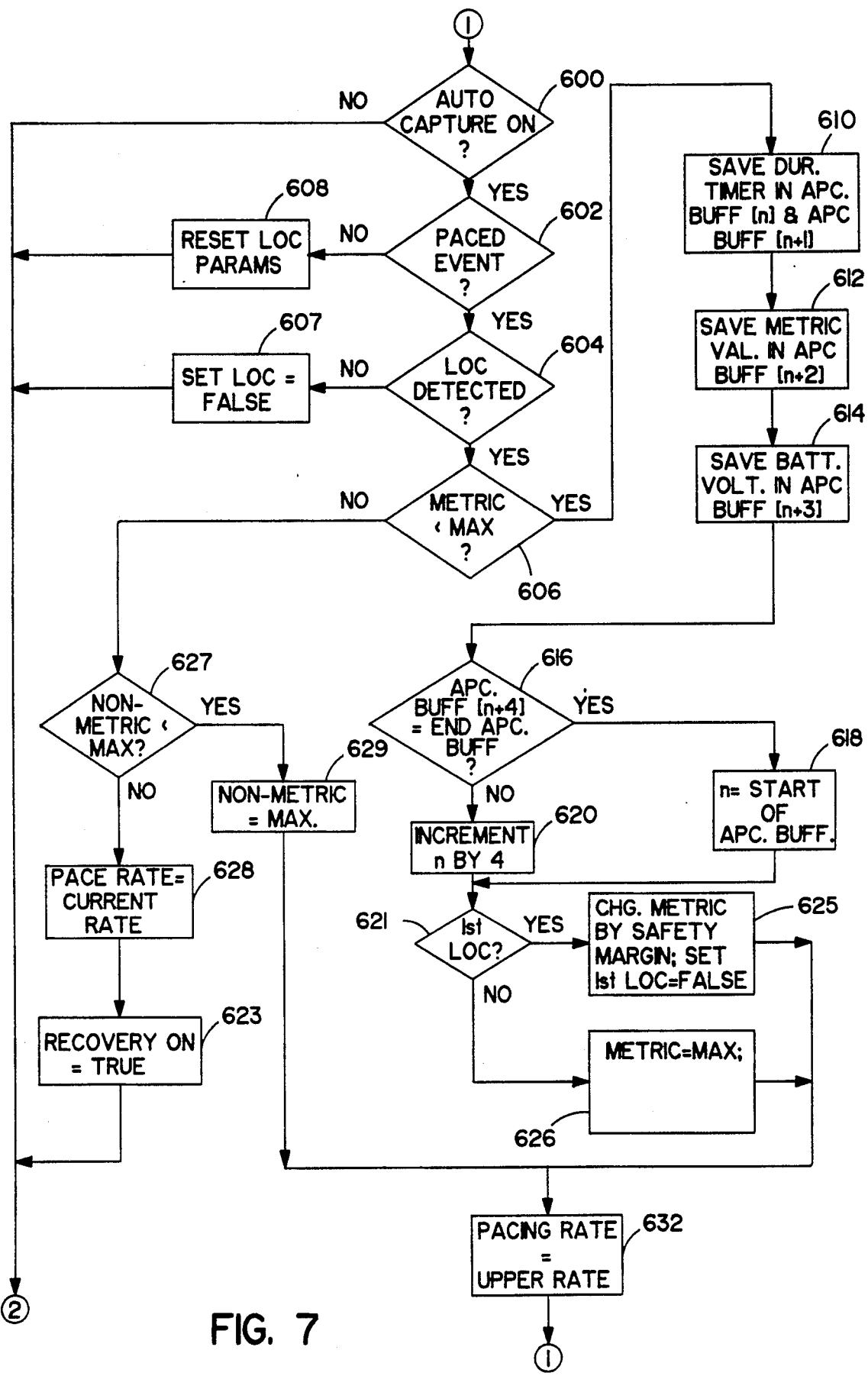
FIG. 7 is a simplified flowchart of the response to loss of capture algorithm and the algorithm for storing the last 32 pulse amplitude or width (PA and PW METRICS) changes and the times of the changes and current battery voltages, resulting from auto capture changes, in memory buffer stages illustrated in FIG. 9 (Map 2)
Figure 8:
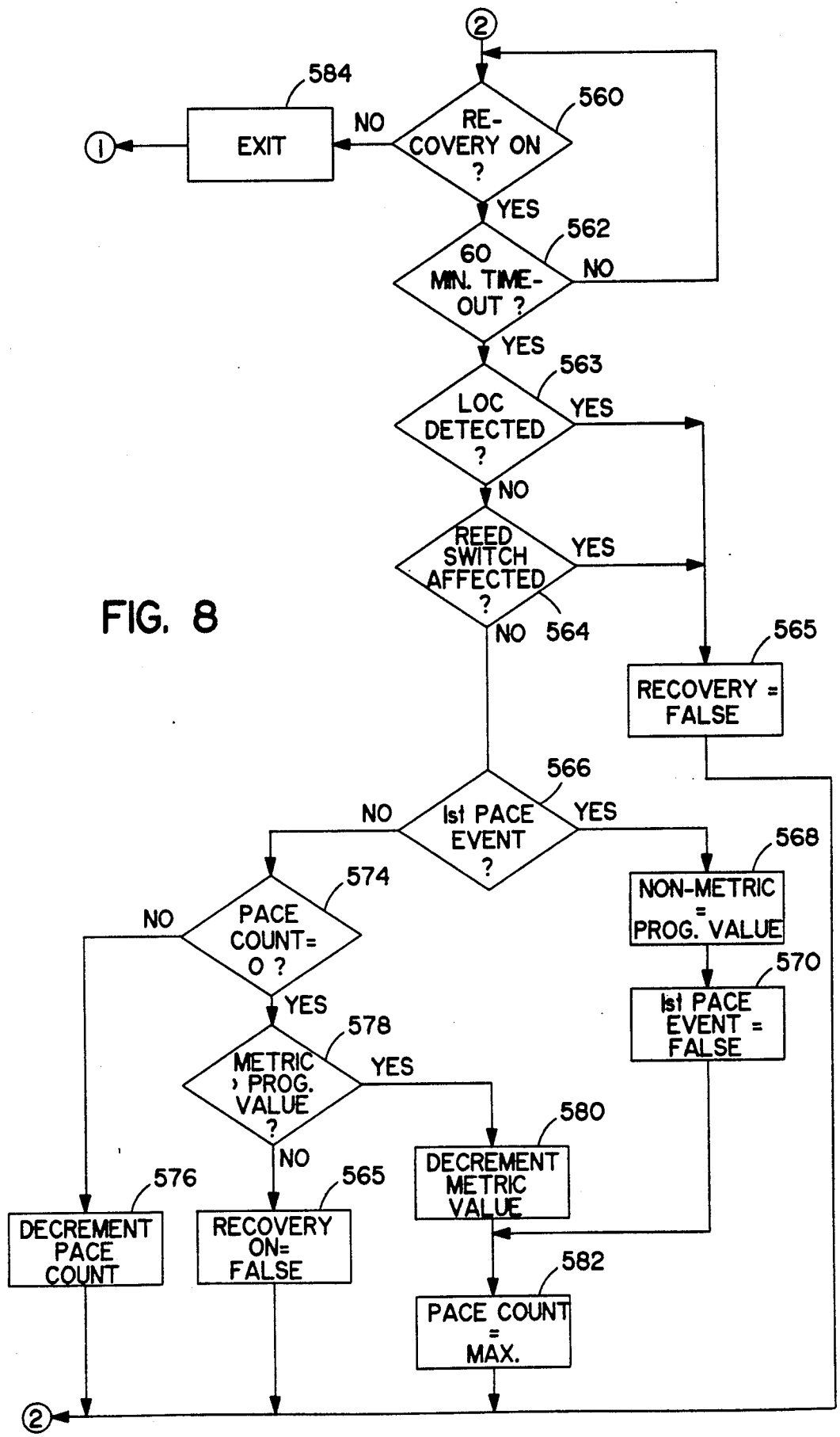
FIG. 8 is a simplified flow chart of the recovery from loss of capture algorithm illustrated in FIG. 6.

FIGS. 7 and 8 illustrate the LOC response and recovery from LOC algorithms.

In FIG. 7, if "Auto-Capture" is programmed on at block 600, each time a paced event occurs LOC is checked in block 604 as described above. A sensed event detected at block 602 at any time resets the LOC algorithm, if it is in the process of increasing pulse energy. At block 607, if LOC is detected, the LOC timeout and recovery algorithm of FIG. 8 is reset.

If all of the conditions indicating LOC are met and if the current operation METRIC is not at its maximum value 10 (MAX), then decision block 606 branches to the LOC algorithm comprising blocks 610–627. If the selected METRIC is at MAX, the decision block 606 branches to examine the NON-METRIC value in block 627.

Blocks 610–620 depict a simplified data storage algorithm for storing the parameters in the manner described in PART XII. C. below. At blocks 621 and 625, when the first LOC event occurs, the safety margin change is made to the prevailing METRIC and the pacing rate is set to the upper rate in block 632. If a second successive LOC is detected, then the METRIC is set to MAX in block 626. Once the METRIC is MAX, a third LOC detected at 604 triggers the setting of the NON-METRIC to MAX in block 629 through decision blocks 606 and 627 and the pacing rate to the upper rate in block 632. If all parameters are at MAX through decision blocks 606 and 627, the pacing rate is returned to the current rate in block 628.

In FIG. 8, a flow chart of the RECOVERY FROM LOC algorithm is depicted. If the METRIC and NON-METRIC values are not at MAX, the RECOVERY- = ON per block. If the one hour timeout depicted in FIG. 6 has expired (block 562) and the reed switch is not affected by a programmer head magnet (block 564), then the NON-METRIC value is returned to the programmed value and sixteen pacing pulses at the METRIC-MAX. value are delivered in accordance with blocks 568, 570, 572, 574 and 576. Thereafter, the METRIC value is decremented and sixteen pacing pulses are provided at the decremented METRIC value through operation of blocks 578, 580 and 582. This process continues until the programmed METRIC value is reached or another LOC occurs, as illustrated in FIG. 6. The RECOVERY FROM LOC algorithm is exited at block 584 and the AUTO-CAPTURE algorithm is recommenced at block 600.

The AUTO-CAPTURE algorithm establishes the current METRIC and NON-METRIC (pulse width or pulse amplitude) values that may be telemetered out on command.

Part XI. Current Value Diagnostics

A. Rate Response Gain and Weighting Coefficients

As described above in reference to FIG. 5 and in PARTs I.A.-C., the modified ACT.GAIN, the PRESS.GAIN and the COEFF is registered in memory registers for telemetry out with the programmed value for each modifier of the rate determination algorithm. Telemetry out is achieved on receipt of an INTERROGATE command specifically identifying CURRENT VALUE data in the manner described in the above-incorporated '407 application.

B. Pulse Width and Pulse Amplitude

The current pulse width and pulse amplitude values prevailing in the AUTO-CAPTURE mode described above in PARTS I.D.-E. and in reference to FIGS. 6-8 are stored in memory location that are likewise interrogatable by an appropriate INTERROGATE command. The CURRENT VALUE PW and PA METRICS are to be distinguished from the PA and PW CHANGES COUNTS stored and read out as one of the sets of programmable diagnostic parameters described hereafter in reference to FIG. 7.

Part XII. Counted Event Diagnostics

FIGS. 7-22 illustrate the storage of counted events for telemetry out on receipt of a specific INTERROGATE command employing the telemetry system of the above incorporated '407 patent. The types of events that are counted and their general descriptions are set forth above.

A. Memory Cell Map

These diagnostics are grouped together in memory to fill the 128 byte buffer according to the six maps illustrated in FIG. 9. These maps are mutually exclusive, that is, only one may be selected to fill the available 128 byte buffer (although additional 128 byte buffers could be included in the pacemaker).

The following table lists the mapping format of the data from the uplink of the diagnostics. Group mapping of the allowed group features does not change the relative offset of the data item in the map. Note that all multibyte counts are stored as:
  Address = Most significant byte
  Address + 1 = Least significant byte

| DIAGNOSTIC | DATA | NO. OF BYTES | OFFSET (D) SEE FIG. 9 |
|---|---|---|---|
| Paced Event Count | Paced Event Counter | 3 | 105 |
| Event Count | Time of Overflow | 3 | 113 |
| | Overflow Flag | 1 | 127 |
| | Total | 7 | |
| Paced Rate Histogram | Bins Counters (Offset 0 = 40-50 ppm bin) (Offset 2 = 50-60 ppm bin) (etc.) | 30 | 0 |
| Histogram | Time of Overflow | 3 | 76 |
| | Overflow Flag | 1 | 127 |
| | Total | 34 | |
| Sensed + Refractory | Refractory Sensed Event Counter | 2 | 108 |
| Sensed Event Counts | Sensed Event Counter | 3 | 110 |
| Event Count | Time of Overflow | 3 | 113 |
| | Overflow Flag | 1 | 127 |
| | Total | 9 | |
| Sensed Rate Histogram | Bins Counters (Offset 38 = 40-50 ppm bin) (Offset 40 = 50-60 ppm bin) (etc.) | 38 | 38 |
| Histogram | Time of Overflow | 3 | 76 |
| | Overflow Flag | 1 | 127 |
| | Total | 42 | |
| Amplitude and Pulse Width Changes | Last 32 Changes (See Note 1) | 128 | 0 |
| | Total | 128 | |
| PVC Counters Histogram | Bins Counters (Offset 116 = 1 PVC bin) (Offset 118 = 2 PVC bin) (etc.) | 8 | 116 |
| Histogram | Time of Overflow | 3 | 124 |
| | Overflow Flag | 1 | 127 |
| | Total | 12 | |
| Rate Trend Analysis | Rate Averages (Offset 0 = Sample Period 1) (etc.) | 60 | 0 |
| | % Paced Averages (Offset 60 = Sample Period 1) (etc.) | 30 | 60 |
| | Gains or Coeffs. (See Note 3) | 11 | 90 |
| | Total | 101 | |
| Sensing Threshold Trend Analysis | SMI (Offset 0 = Sample Period 1) (etc.) | 64 | 0 |
| | Total | 64 | |
| Projected Rate Trend Analysis | Rate Averages (Offset 0 = Sample Period 1) (etc.) | 60 | 0 |
| | Total | 60 | |
| Optimization Trend Analysis | Last 52 Gains or Coeffs. and Day (See Note 3) | 104 | 0 |
| | Total | 104 | |

NOTE 1:
Data will be placed into the buffer starting at offset 0. First, a 16-bit count will be saved which will be equal to the current value of the diagnostic duration counter divided by 4. Next, the value the programmed METRIC changed from and battery voltage will be saved.

The value of the PW METRIC is the "measured" value. The PA value must be calculated from the programmed pulse amplitude and battery voltage.

NOTE 2:

Any change of ACT.GAIN, PRESS. GAIN or COEFF will be placed into the buffer in sequence starting at the first day of sampling. Sensor coefficients values will have a value range of 0 through 10H and gain values will range from 2XH through CXH.

NOTE 3:

Changes in ACT.GAIN, PRESS.GAIN or COEFF will be placed into the data area following the day number of the change. The day value will be the number of days since the start of the diagnostic. The gain or coefficient values may be identified as defined in NOTE 2.

B. System Time Clocks/Duration Counters

As can be seen above, data indicating the time of overflow of counters and bins is also stored for certain of the diagnostics. The basic 2-second and 24-hour optimization clocks referred to above are derived from the system clock in digital controller/timer circuit 132 which establishes four clocks used to "time stamp" events and turn diagnostic functions on and off. The user may select from among the above identified diagnostics that are capable of being "time stamped" with the Time of Overflow as well as the time when diagnostics are enabled and the duration of enablement.

The DIAGNOSTIC clock is a 24-bit clock with minute resolution used to represent up to 20 years of time. An implicit "post" time of 00:00 hrs is assumed for all external programmers intending to communicate with this clock. Current time is defined as the number of minutes between now (date/time) and the "post" date/time. Upon a loss of power, the clock will be reset to 00:00. The clock is formatted as a 24 hour clock with a resolution of 1 minute and an accuracy of $+/-54.1$ min/year.

The DIAGNOSTIC clock can be "set" via programming commands to conform with clock time. The clock is set immediately after the appropriate telemetry commands have been received. This allows features/functions to be synchronized to specific times of the 24-hour day.

The START TIME at which an algorithm or function is enabled can be set by programming commands. The function or algorithm is enabled when the clock time matches the START TIME. START TIME is a 24-bit value representing the number of minutes between the post date and time and the desired date/time a selected diagnostic function is to begin. A start time of "NOW" is equal to a value of 00 00 (Hex).

If this value is not set or is less than the current time, designated diagnostic functions are not enabled and duration is ignored. Only one START TIME may be set. The maximum START TIME allowed is six months (ensured by programing peripheral).

The DURATION that an algorithm or function is enabled is controlled via programing command. A selected algorithm or function is disabled when the DURATION interval expires. This command sends an "end time" value for disabling a diagnostic function. End time is a 24-bit value representing the number of minutes between the post date and time and the desired date/time a selected diagnostic function is to stop.

The programming peripheral will always ensure a set DURATION value is programmed. The designated diagnostic functions will end when any overflow condition occurs. Only one DURATION may be set. The maximum DURATION allowed is six months (ensured by programming peripheral).

C. Pulse, Width or Amplitude Changes

Referring back to FIG. 7, it also depicts the algorithms described generally above in PART I, J, for storing the last 32 value changes (due to Autocapture) of the programmed PA or PW METRIC recorded along with the time of change and the current battery voltage (at the time of change). The value recorded is the "measured" or stretched value being changed from. This feature is enabled via START time and a DURATION of six months may be set for the storage. Over that period, the contents of the buffer illustrated in FIG. 9 are filled with the last 32 value changes on a recirculating, continuous basis as long as the autocapture algorithm is programmed on.

In decision block 600, the status of Autocapture programing is determined and if it is programmed ON, then if a paced event results in LOC, then the status of the METRIC is compared to its MAX, value in decision block 606. If it is not a paced event, then a sensed event has occurred; therefore, the parameters needed to track the performance of the loss of capture are reset since the heart has contracted.

If the METRIC is less than MAX., then the current time is saved in block 610 along with the "changed from" METRIC value in block 612 and the then current battery voltage in block 614. The APe. BUFF entry for the amplitude or pulse width changed comprises 32 bits divided into 4 bytes designated n, n+1, n+2 and n+3. The data is shifted in blocks 610, 612 and 614 into the respective bytes of the APC. BUFF. Note that APC. BUFF consists of 128 bytes total (FIG. 9).

At decision block 616, the status of the APC. BUFF is checked and if it is full, then the next entry will occur at the start of the buffer as indicated by block 618 overwriting the information previously stored there. Otherwise, it is incremented by 4 as shown by 620 to the next available location for data storage.

Figure 10:
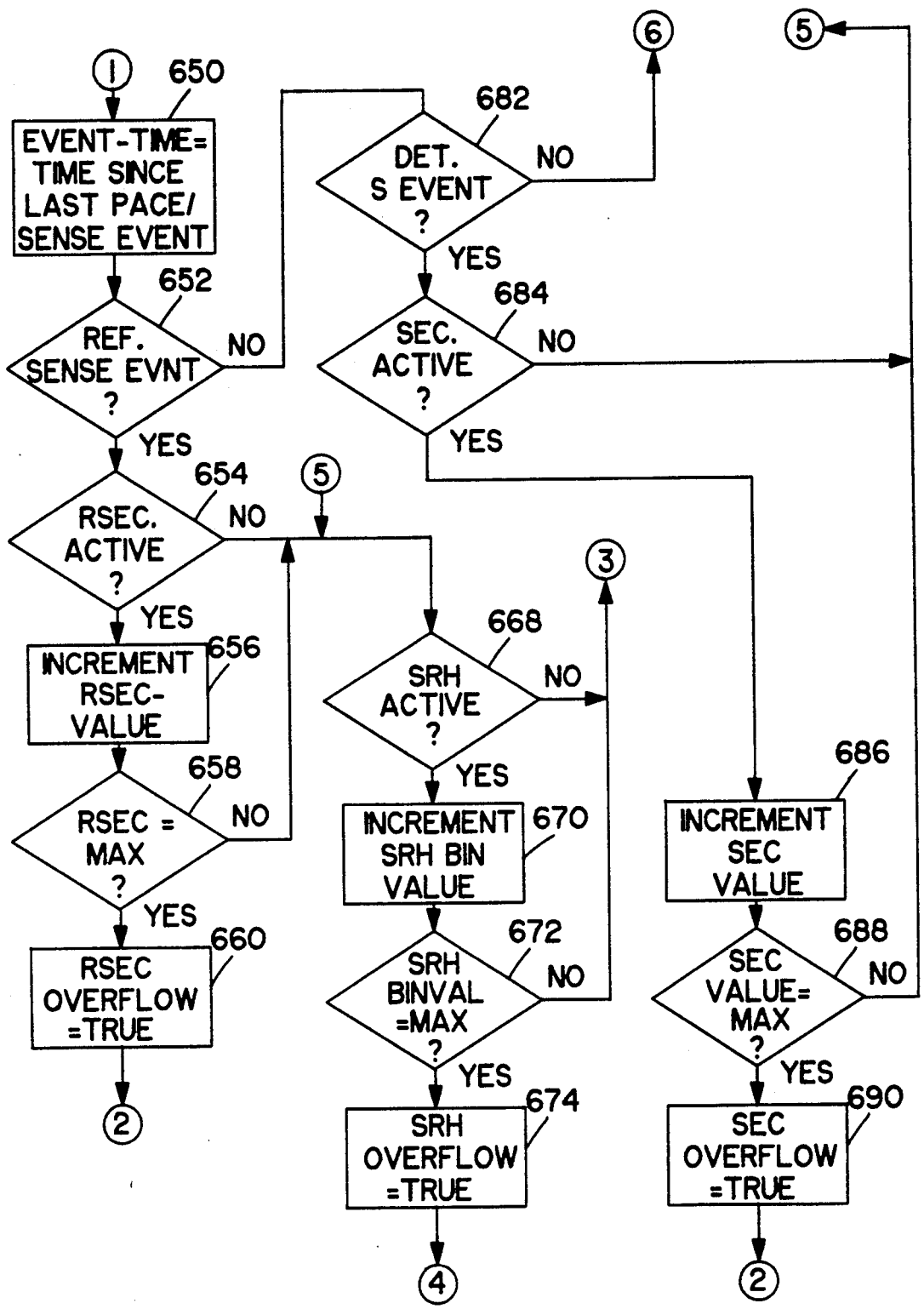

D. Refractory Sensed Event Count/Sensed Event Count/Sensed Rate Histogram/Paced Event Counts/Paced Rate Histogram Turning now to FIGS. 10 to 13, they illustrate the storage of these events described above in PARTS I. F.-I. which may be separately programmed. FIG. 10 relates to the sensed events and rate histogram, FIG. 11 relates to the paced events and rate histogram, and FIGS. 12 and 13 relate to the time of overflow event recording for the event in histogram counters. The general operation of the flow charts of FIGS. 10 through 13 is described above in PART I.

In reference to FIG. 10, it illustrates the recording of refractory sensed events and normal sense events for storing those events as well as the time of overflow of each counter. At block 650, the interval since the last event which was terminated by a sensed event, which will correspond to a rate for looking up the proper histogram bin to increment. At decision block 652, if the sensed event falls within the refractory period since the preceding sensed or paced event, then the refractory sensed event counter (RSEC) is incremented in block 656 if it is activated in accordance with decision block 654. The RSEC event count is checked against the maximum count in decision block 658, and if the maximum has been reached, then the RSEC overflow is set to "true" in block 660. The setting of RSEC overflow to "true" directs the program to FIG. 11 where the RSEC.ACTIVE and SEC.ACTIVE are set to false in block 662. At the same time, the PEC.ACTIVE is also set to false in block 664 and the time of overflow (TOO) is set to equal the current time in block 666. All of the values including the TOO are stored in memory in the locations designated in FIG. 9.

Referring back to FIG. 10, if the RSEC or refractory sensed event counter is not active, then the status of the sensed rate histogram (SRH) function is checked in decision block 668. If the SRH is active, then the appropriate SRH bin value is located using event time and is incremented in block 670. Each time a SRH bin is incremented, the bin value is compared to the maximum value in decision block 672 and if one of the bin values reached maximum, then the SRH overflow is set to "true" in block 674, and the algorithm shifts to the flow chart depicted in FIG. 12. If the SPa is not active in block 668 or if the SRH.BIN.VAL is not MAX, then the algorithm shifts to FIG. 13A and processes the next event. In FIG. 12, once the SRH overflow is set to true, then the SRH.ACTIVE is set to "false" in block 676. At the same time, the pacing rate histogram is deactivated as the PRH.ACTIVE is set to "false" in block 678.

Thereafter, the time of overflow of the histogram is set to the current time in block 680 and the next event is processed in FIG. 13A. The TOO.HIST recorded in either case is the one minute clock elapsed time from the last interrogation at the most recent patient follow-up as described above.

Referring back to FIG. 10, if a detected event is not a refractory sensed event, then it is examined in block 682 to make certain that it is a detected sensed event and if so the status of the sensed event counter is checked in the decision block 684, labeled SEC.ACTIVE. If the sensed event counter is not active, then the program switches back to the sensed rate histogram algorithm blocks 668–674 where the sensed event may be employed to increment the SRH bin value.

On the other hand, if the sensed event counter is active, then its value is incremented in block 686. The incremented value is compared to the maximum value in block 688 and if the SEC value exceeds the maximum then the SEC overflow is set to true in block 690. At this point, the program switches over to the program depicted in FIG. 11 with the result that the sensed and paced event counters are turned off in blocks 662 and 664, respectively, the time of overflow is set to the current time in block 666 in the manner previously described, and the next event is processed in FIG. 13A.

Referring now to FIG. 13, in the event that the event is not a detected sensed event, then it is examined in block 692 to determine whether or not it is a scheduled paced event. If it is, then the pace event counter is active as determined by block 692, then the PEC value is incremented in block 694. In block 696, the PEC value is compared to MAX., and if it equals MAX., then the PEC overflow is set to "true" in block 698. Again, the program switches to the algorithm depicted in FIG. 11 where the SEC.ACTIVE, the RSEC.ACTIVE and the PEC.ACTIVE are set to "false" and the time of overflow of the event is again recorded in block 666.

If the PEC value is not at MAX. or if the PEC is not active, then the detected paced event is directed to decision block 700 where the status of the pacing rate histogram (PRH) feature is examined. If the PRH is active, then the appropriate PRH bin is located using EVENT.TIME and is incremented in value in block 702 and its value is compared to MAX. in block 704. If one of the bins of the PRH counters is full, then the PRH overflow is set to true in block 706 and the algorithm again switches to the algorithm of FIG. 12 where the SRH.ACTIVE and the PRH.ACTIVE flags are set to "false" and the time-of overflow or the TOO.HIST is recorded in block 680. If the PRH is not active at block 700 or the PRH VALUE is not MAX in block 704, the next event is processed in FIG. 13A.

E. Rate Trend Analysis

As described above in PART I.L. when rate trend analysis (RTA) is programmed on and enabled by way of a START time, the pulse generator monitors the average pacing rate, the percent paced, the ACT.GAIN, PRESS.GAIN and the COEFF over a programmed time interval. The physician can program the total time of the calculated averages and the selected gain values and coefficient values over the time periods or segments described above. As shown in FIG. 9, only a certain amount of memory is available to store these values regardless of the segment programmed, and so the resolution of data storage varies as described above in PART I.

Figure 14:
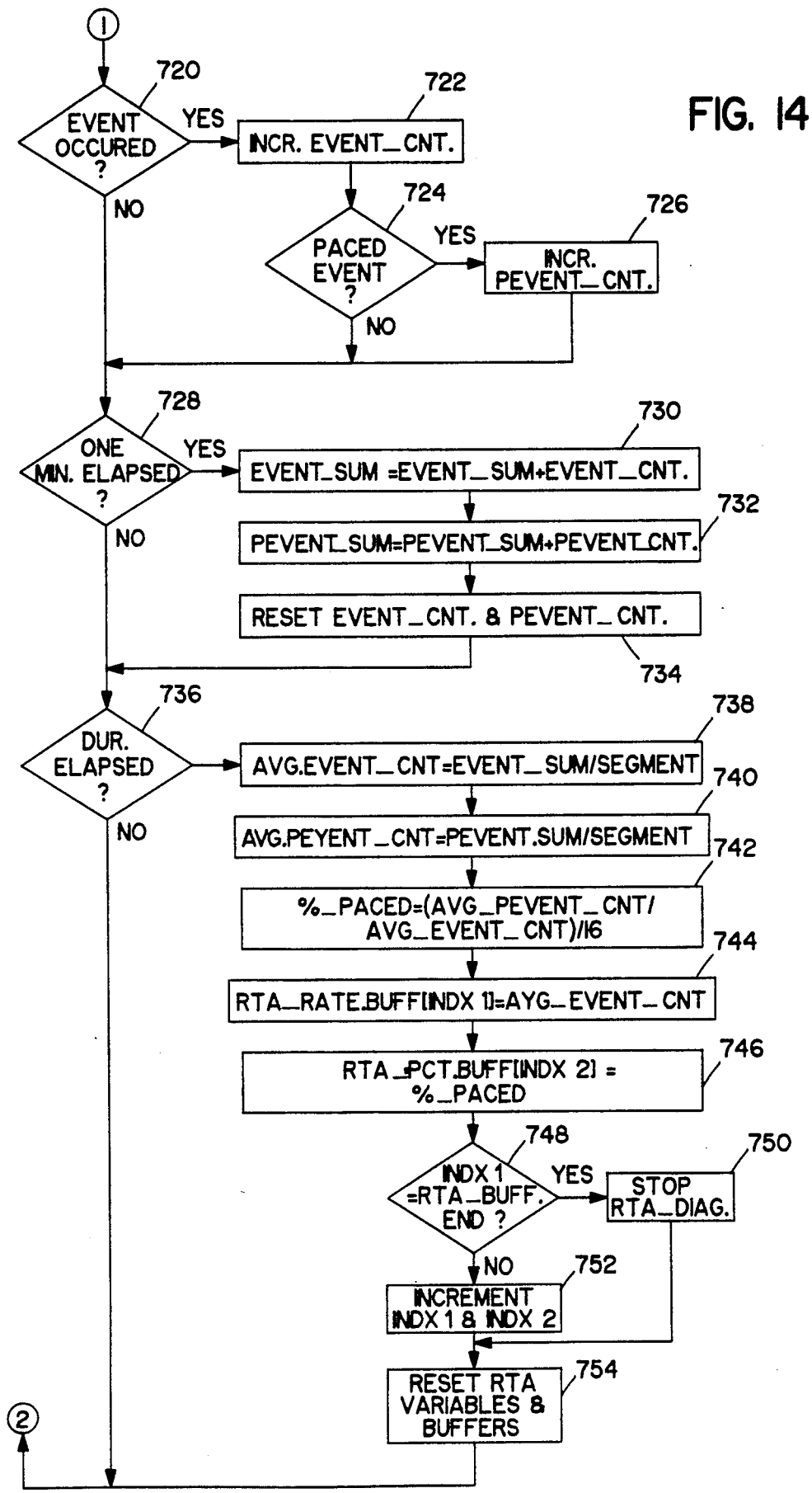
FIG. 14 is a simplified flow chart of the rate trend analysis algorithm for storing average pacing rate and percent paced diagnostic data over programmed periods in memory buffer stages illustrated in FIG. 9 (Map 3)

The rate trend analysis algorithm is depicted in FIG. 14 in conjunction with the FIG. 15 depiction of the storage of the associated ACT.GAIN, PRESS.GAIN and the COEFF values. In FIG. 14, the occurrence of an event is determined in decision block 720 and the event counter is incremented in block 722. If the event is a paced event, as determined in decision block 724, then the PEVENT.CNT is incremented in block 726. This incrementing of the counters is done on a beat by beat basis and the average is determined each minute.

When one minute has elapsed in decision block 728, the algorithm switches to summing the events and paced events in blocks 730 and 732. The EVENT.SUM is updated by adding EVENT.CNT thereto, as follows: EVENT.SUM = EVENT.SUM + EVENT.CNT in block 730. PEVENT.SUM is similarly updated by adding PEVENT.CNT thereto, as follows: PEVENT.SUM = PEVENT.SUM + PEVENT.CNT in block 732. After the EVENT.SUM and the PEVENT.SUM are calculated in blocks 730 and 732, the values are stored and the EVENT.CNT and PEVENT.CNT values of blocks 722 and 726 are reset to zero.

Turning now to decision block 736, it times out the duration, which may be programmed to either one minute, 32 minutes, 128 minutes or 256 minutes, to set the resolution of the average data described above. Thus, if a physician programs in a total time of 10 days to derive 60 sets of data, then each data set has a resolution of the average of 256 minute segments. Assume, for example, that the 256 minutes have elapsed. A set of data is then determined in blocks 738–746. In block 738, the average event count for the elapsed duration is calculated as the value calculated in block 730 divided by the segment number programmed in, that is 1, 32, 128 or 256. Similarly, the average paced event count is calculated in block 740 by dividing the value of block 732 by the programmed segment.

In block 742, the percent paced value is determined by dividing the average paced event count determined in block 740 by the average event count of block 738 and then dividing that fraction by 16 to arrive at the ranges 0–15 set forth in PART I.L. above.

As described in PART I.L., when the rate trend analysis feature is enabled, the pulse generator monitors the average pacing rate (RTA) and percentaged paced (% PACED) and provides 60 sets of data representing each in accordance with the programmed-in total duration and segment. RTA data is stored as 60 bytes while % PACED is stored as 60 half-bytes (nibbles). Blocks 744 and 746 provide for the transfer of the calculated values into the 60 bytes and 30 bytes, respectively. INDX1 addresses bytes for the rate averages values and INDX2 addresses nibbles for the percent paced values.

In block 744, the RTA.RATE BUFF [INDX1] is set to AVG.EVENT.CNT. In block 746, the RTA.PCT. BUFF [INDX2] is set to the %.PACED value. Thus, the rate trend analysis rate and percent pacing at the time out of each of the programmed-in durations is stored in the buffer locations indicated on the memory map of FIG. 9 (Map 3). Simultaneously, although not shown specifically in FIG. 14, it will be understood that the then prevailing ACT.GAIN and PRESS.GAIN and the COEFF values indicated above in Part I are stored.

Each time a data value is entered in the buffer, its status is checked in block 748 and if the INDX1 is the last or the end byte of the buffer, then the RTA diagnostic is stopped in block 750. If the last byte has not been reached, then the pointer is incremented in block 752 to the next byte to receive the calculated data on the duration lapse determined in block 736. In either case, the RTA variables and buffers are reset in block 754 on loading the RTA.RATE and the RTA.PCT values into the buffers and the program loops back to the start.

As described above in PART I, when the rate trend analysis feature is enabled, the pulse generator also monitors the ACT.GAIN, PRESS.GAIN and the rate response sensor coefficient COEFF over the programmed duration. Since these values may be changed on a daily basis, no value is stored if the segment is programmed to one hour and one value is stored for each of the days over the monitored period.

Turning now to FIG. 15, it illustrates in a flow chart, the algorithm employed to store that data on a daily basis. At decision block 760, the change status of the gain and coefficient values of FIG. 5 are checked to determine if any of the values have changed. If they have not changed, then the message NO CHANGE is set in block 762 to represent the letter "A" thereafter in block 764 where the rate trend analysis gain change buffer [INDX] is set to A, which in this case is equal to "no change". However, if a change is noted in block 760, then the type of change is examined in block 762. If it is a gain change, A is set to the current activity gain or ACT.GAIN and the contents of the buffer A are shifted left by four bits and the pressure gain or PRESS.GAIN value is recorded in the four least significant bits of the eight-bit buffer A in block 770. Thereafter, the RTA.GC. BUFF [INDX] is set to A in block 764.

However, if only the COEFF value has changed then the eight-bit memory cell A is loaded with the COEFF value in block 772 and that value is loaded into the RTA.GC BUFF [INDX] in block 764. Thereafter, the INDX buffer pointer is incremented in block 774 and the flags and counters are reset in block 776.

F. Projected Rate-Trend Analysis

As indicated above in PART I.N., the projected rate-trend analysis or PRTA is enabled by a START TIME and the pulse generator monitors the projected rate response pacing rate based on one or both rate response sensors, the ACT.GAIN, PRESS.GAIN and the rate response sensor coefficient COEFF in a data format that is identical to the rate-trend analysis, except that the percentage pace values are not calculated and the sampling rate is changed to two seconds from one second. If programmed ON, the PRTA algorithm may be employed to store data over time which represents the pacing rate that would have been realized if one or both of the activity and pressure sensors, $S_1$ and $S_2$, had been programmed ON.

In other words, if only one or the other of the sensors is programmed on, then the PRTA algorithm may be employed to provide a set of data in parallel with the actual RTA data to show the physician how the pulse generator would have behaved if the other sensor had been programmed ON. Similarly, the PRTA algorithm may be employed when neither sensor is programmed ON to control the pacing rate.

Figure 16:
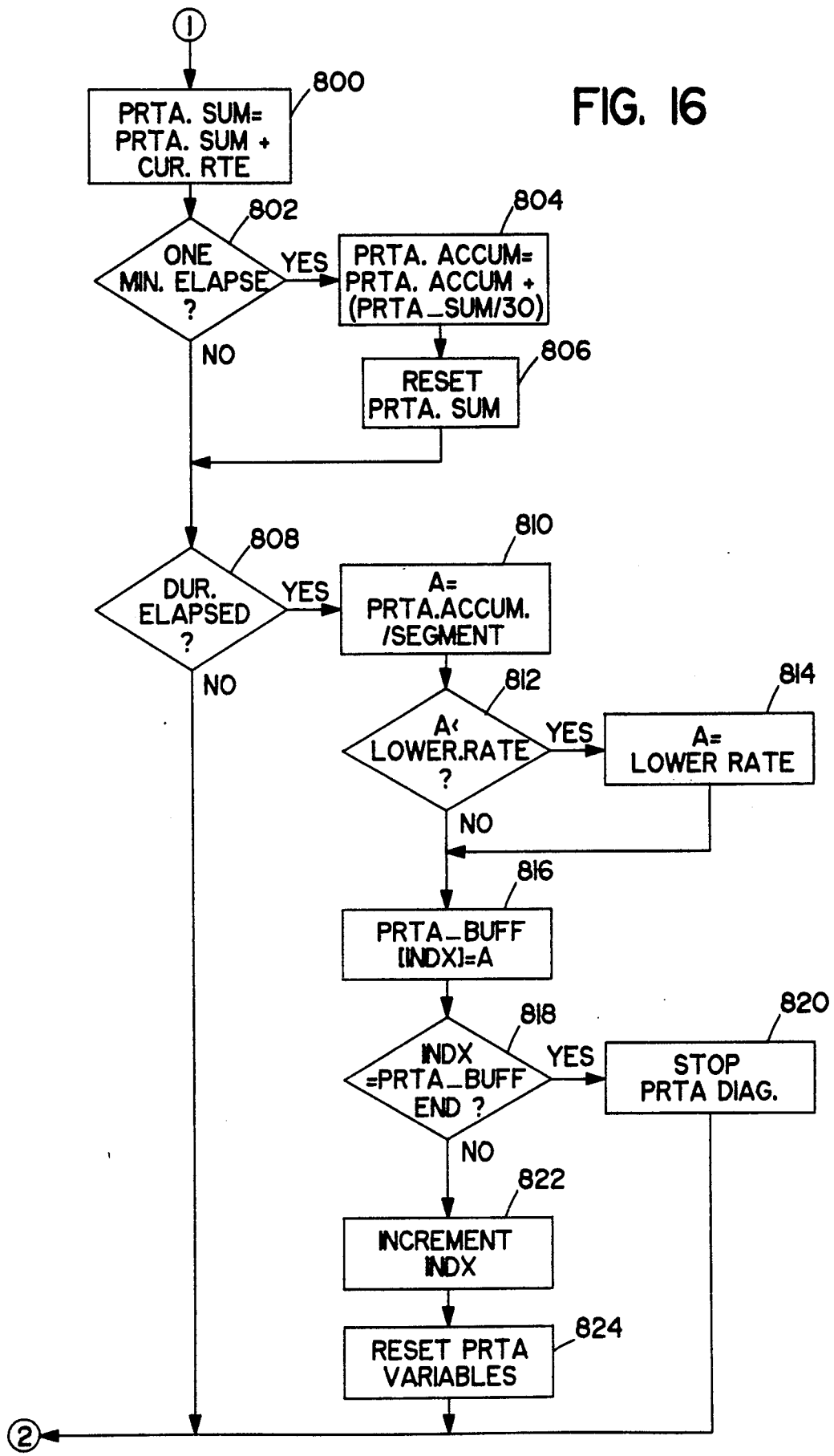
FIG. 16 is a simplified flow chart of the projected rate trend analysis algorithm for storing projected average pacing rates based on one or both of the RCP sensors, when those sensors are programmed OFF, in memory buffer stages illustrated in FIG. 9 (Map 6)

As described above in PART XII.B., the rate determination based on the sensor output values is determined every two seconds. Turning now to FIG. 16, at block 800, the PRTA.SUM is updated to a value corresponding to PRTA.SUM plus the current rate CUR.RTE. In other words, the current rate values are summed in block 800 and, after the lapse of one minute, the PRTA.ACCUM is incremented in block 804 by dividing the PRTA.SUM value by 30 and adding it to the previous PRTA.ACCUM value. Thereafter, the PRTA.SUM value block 800 is reset in block 806 to restart the summation and accumulation on a minute-by-minute basis.

In the same manner as described with respect to the RTA algorithm of FIG. 14, the PRTA algorithm may be programmed to derive the 60 average values over a one hour, one day, five day or ten day period in average segments of 1, 32, 128 and 256 minutes, respectively. In FIG. 16, the programmed duration is checked in block 808 and if it has lapsed, then an eight-bit register A is set to the PRTA.ACCUM value divided by the corresponding segment number or 32, 128, or 256 in block 810.

Either the value A or the programmed lower rate value will be stored in the PRTA.BUFF [INDX] in accordance with blocks 812-816. It will be appreciated that in certain circumstances, the PRTA algorithm may derive a pacing rate over the particular segment which is actually lower than the programmed in lower rate that the pacemaker is currently operating at. For example, the physician may set the patient's lower rate at a rate which in fact exceeds the rate required, at least in accordance with the sensor derived rate algorithm. In decision block 812, the value A is compared to the lower rate value. If it is less than the lower rate value, then the value A is switched to the lower rate value in block 814 and it is entered into the PRTA buffer at the appropriate memory location represented by the INDX.

In decision block 818, the INDX in which the preceding value A was entered is checked to determine whether or not it is the last stage of the PRTA buffer. If it is, then the PRTA diagnostic is stopped in block 820 and the program no longer accumulates the PRTA.SUM values in block 800. However, if the last stage of the buffer is not yet reached, then the INDX pointer is incremented in block 822 and the PRTA variables are reset in block 824.

G. Optimization Diagnostic

As described above in PART I.O., the last 52 changes in ACT.GAIN, PRESS.GAIN or COEFF may be saved as well as the day that the changed occurred. As described above in conjunction with FIGS. 4 and 5, optimization is conducted on a daily basis. The algorithm for storing these values and the day of change is depicted in the flow chart of FIG. 17. The OTA buffer is an 8 bit recirculating buffer which means that it stores only the immediately preceding 52 sets of data. In decision block 830, the status of the blocks 505, 527, 523, 517, and 513 are monitored, and if one of those blocks is set to "true", then the OTA BUFF [INDX] is set to that day's date value in block 832. The day's date is a system clock number that may be decoded to provide the actual date to the peripheral programmer.

In block 834, the INDX is incremented and the status of the block 505 of FIG. 5 with respect to a true gain change is determined in block 836. If a gain change is true, then the OTA.BUFF (INDX 4BIT) is set to the ACT.GAIN in block 838. In other words, if the activity gain has been modified then the value is stored in the upper 4 bits of the OTA buffer designated by INDX.

Similarly, if the pressure gain is changed, then the PRESS.GAIN is stored in the lower 4 bits of the OTA buffer designated by INDX in block 840. If the change was in the COEFF value, then it is stored in the OTA buffer designated by INDX in block 842.

In either case, after the value is loaded into the memory location addressed by INDX, the decision block 844 determines whether or not the end of the buffer has been reached. If the last memory location has been filled, then the first location is enabled to be written over in block 846. Otherwise, the pointer is incremented to the next memory address in block 848. After the optimization, the GAIN, CHG and COEF.CHG flags are reset in block 850. The data is stored in the memory map and location as depicted in FIG. 9 and as described above.

H. Sensing Threshold Analysis

As described above in PART I.M., when the sensing threshold trend analysis or STA is enabled, the pulse generator monitors the average peak sense value over a programmed time interval. The programmable time intervals extend from one hour to six months as described above in PART. I and either 60 or 64 values may be stored in the locations indicated on the memory map of FIG. 9 in 1, 32, 128, 256, and 4096 minute Segments. Sampling is conducted at 4 second intervals except when the one hour time interval is selected or sampling is conducted on a beat by beat basis. The 4 second intervals are set by the system clock described above. Depending on the patient's underlying rhythm, anywhere from 0 to perhaps 10 sensed R-waves may fall within the 4 second interval. The peak sensed event is the highest level of the detected R-wave converted to a digital value by an A/D converter in the digital controller/timer circuit 132 which receives the output of the sense amplifier 146 as shown in FIG. 1. Such peak detecting circuitry is well known in the prior art. An example of a system by which the sensing threshold of an implanted pacemaker may be automatically initialized in conjunction with an external programmer is set forth in commonly assigned, copending U.S. patent application Ser. No. 567,372, filed on Aug. 14, 1990, to Tommy D. Bennett et al., which is herein incorporated by reference.

Figure 18:
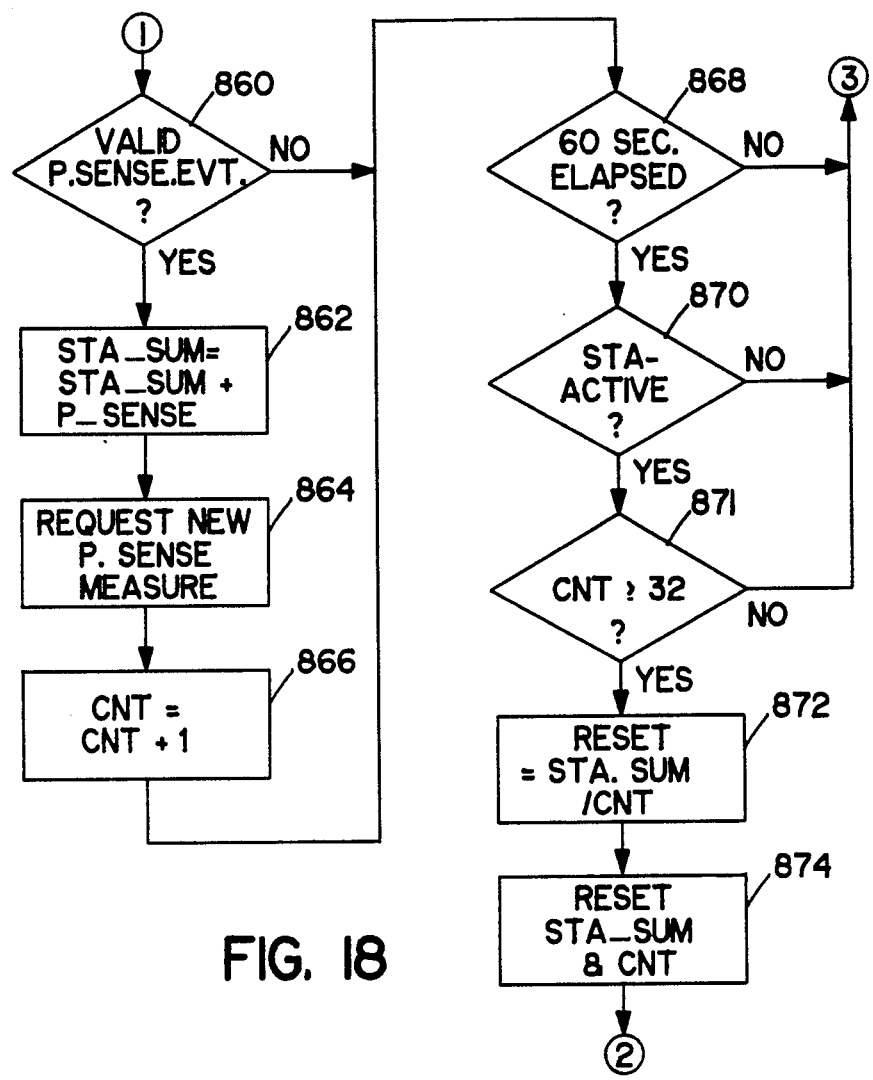
FIGS. 18-20 collectively are a simplified flow chart of the sensing threshold trend analysis algorithm for storing average peak sense signal values over a programmed time interval in memory register stages illustrated in FIG. 9 (Map5)
Figure 19:
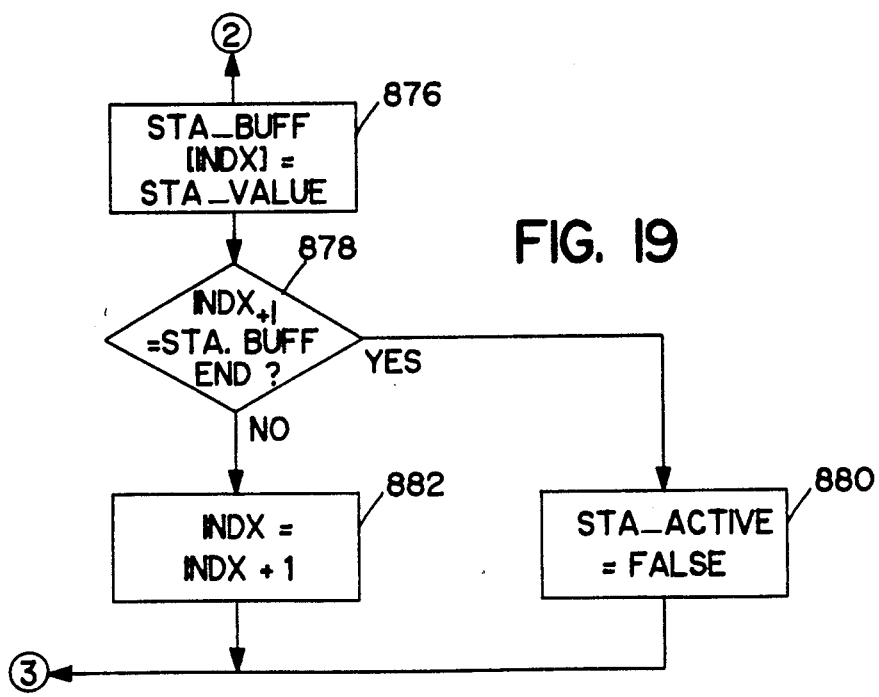
Figure 20:
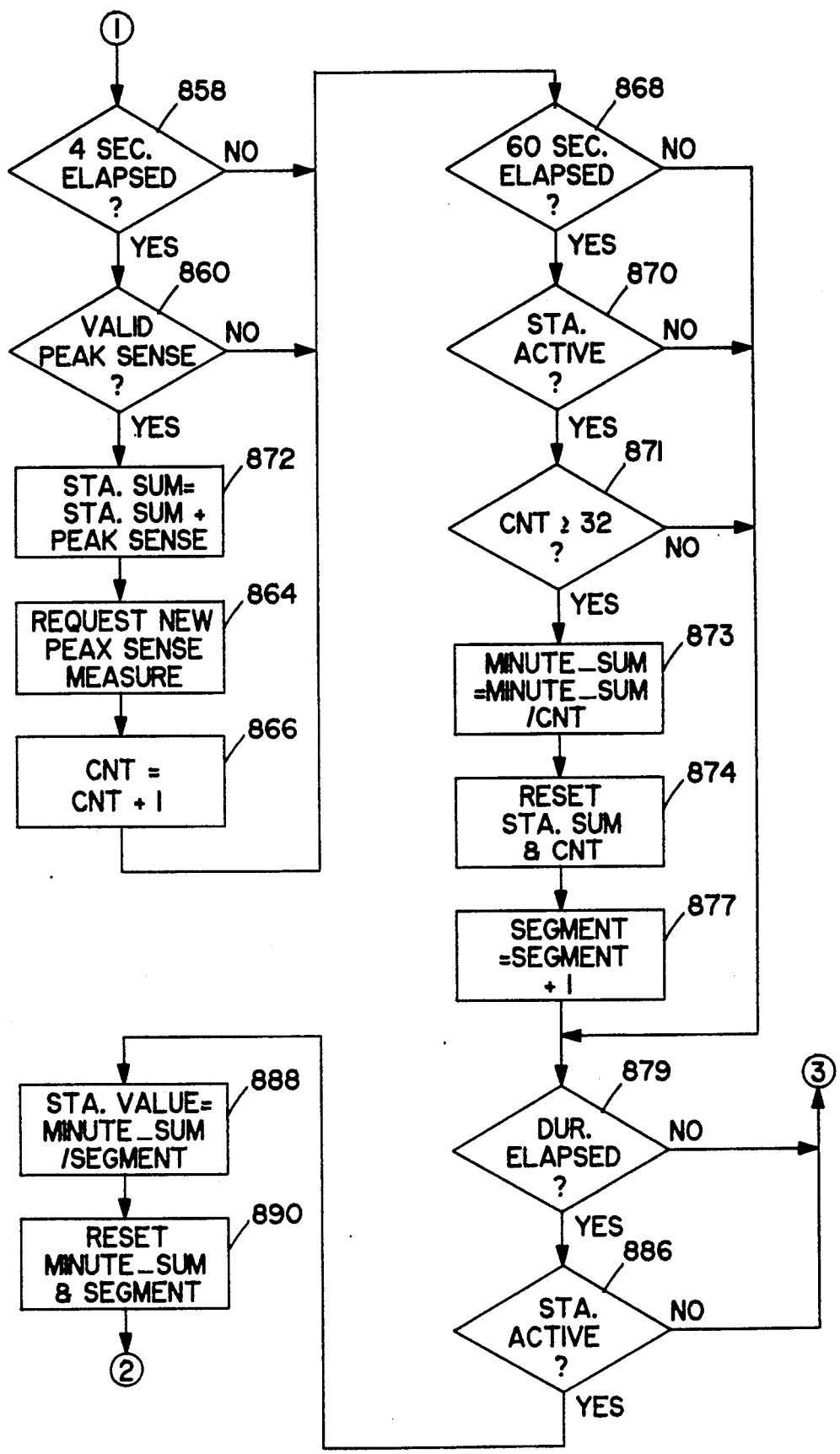

The STA diagnostic algorithm is depicted in the flow charts of FIGS. 18-20. FIG. 181 illustrates the calculation of the 60 one minute averages of the peak sense values on a beat by beat basis deriving the one hour duration STA diagnostic data set. FIG. 19 illustrates how that data set is stored in the memory locations depicted in the memory map of FIG. 9. FIG. 20 illustrates the storage of the STA diagnostic values over the longer durations applying the longer segments providing the 60 averages of the peak sense values sampled at the 4 second intervals described above. The data derived in the algorithm depicted in FIG. 20 is stored in the same fashion as shown in the algorithm depicted in FIG. 19.

In FIG. 18, each time a valid peak sensed event occurs, decision block 860 directs the summation of the peak sense value with the preceding sum, that is STA.-SUM in block 862. Thereafter, another peak sense measure is requested in block 864 and an event counter is incremented in block 866 such that the current count CNT is incremented from the last count CNT by 1.

In the interim between valid peak sense events or during the steps depicted in block 862-866, the 1 minute timer is counting out and when 60 seconds have elapsed in decision block 868, the status of the sensing threshold trend analysis is examined in block 870. If it is ACTIVE, and if the counter has a current count of at least 32 peak sense event (block 871), then the STA.VALUE is calculated in block 872. The STA.VALUE is an average calculated by dividing the STA.SUM value of block 862 by the total current count CNT stored in block 866. Thereafter, the values in blocks 862 and 866 are reset in block 874 and the algorithm continues in FIG. 19 with the Storage of the STA.VALUE in the STA.BUFF at location INDX.

In FIG. 19, the STA.VALUE is shifted into the memory location at INDX. In decision block 878, the index is incremented by one and its value is compared to the last memory location of the buffer. If the end of the buffer is reached, then the STA.ACTIVE status is set to "false" in block 880. This sets the STA.ACTIVE to NO in block 870 in FIG. 18. If the STA buffer is not filled, then the index is incremented by 1 in block 882.

Turning now to FIG. 20 it incorporates several of the steps of the algorithm illustrated in FIG. 18 to derive the one minute average values which are them averaged over the 32, 128, 256, and 4096 minute segments to derive the 60 or 64 values over the durations from 1 day to 6 months described above. At the outset, the decision block 858 examines whether or not the 4 second sampling interval has elapsed. A valid peak sense value, in these programmed segments, is derived from the non-refractory sensed events occurring between the 4 second intervals. Then the valid peak sensed values are processed in blocks 862 through 871 in the manner described above. This portion of the algorithm does not derive the STA.VALUE but instead derives a MINUTE.SUM for further averaging over the segment time in block 873 which is labeled to reflect the derivation of the MINUTE.SUM. In block 877, the segment counter is incremented to reflect the SEGMENT.

At the same time this processing is taking place, the DURATION timer is timing out and when the duration lapses in decision block 879, the status of the STA buffer is checked in decision block 886. If the STA buffer is not filled, the STA.VALUE is set to the MINUTE.SUM divided by the SEGMENT number in block 888. The MINUTE.SUM in block 873 and the SEGMENT in block 877 are then reset in block 890. Thereafter, the algorithm shifts to the algorithm depicted in FIG. 19 to store the STA.VALUE in the STA.BUFF in the manner described above.

In this fashion, the data of the sensing threshold trend analysis is accumulated over the program duration in the manner described in PART I.M. above.

I. PVC Count HistoGram

Premature ventricular contractions or PVCs are defined as naturally occurring ventricular contractions (i.e., sensed events) that follow a preceding paced or sensed event within a certain time window which is suggestive that the ventricular contraction is ectopic, rather than sinus in origin, or is the product of an atrial contraction elicited in a retrograde conduction of the immediately preceding ventricular (usually paced) event. PVCs falling outside the refractory period inhibit the WI pacemaker from pacing. Runs of two or more successive PVCs can additionally result in reduced cardiac output uncomfortable to the patient and lead to sustained ventricular tachycardia and in certain circumstances to more malignant arrhythmias. Monitoring of the frequency of occurrence of single and runs of PVCs is desirable in devices of the sort described herein.

Figure 21:
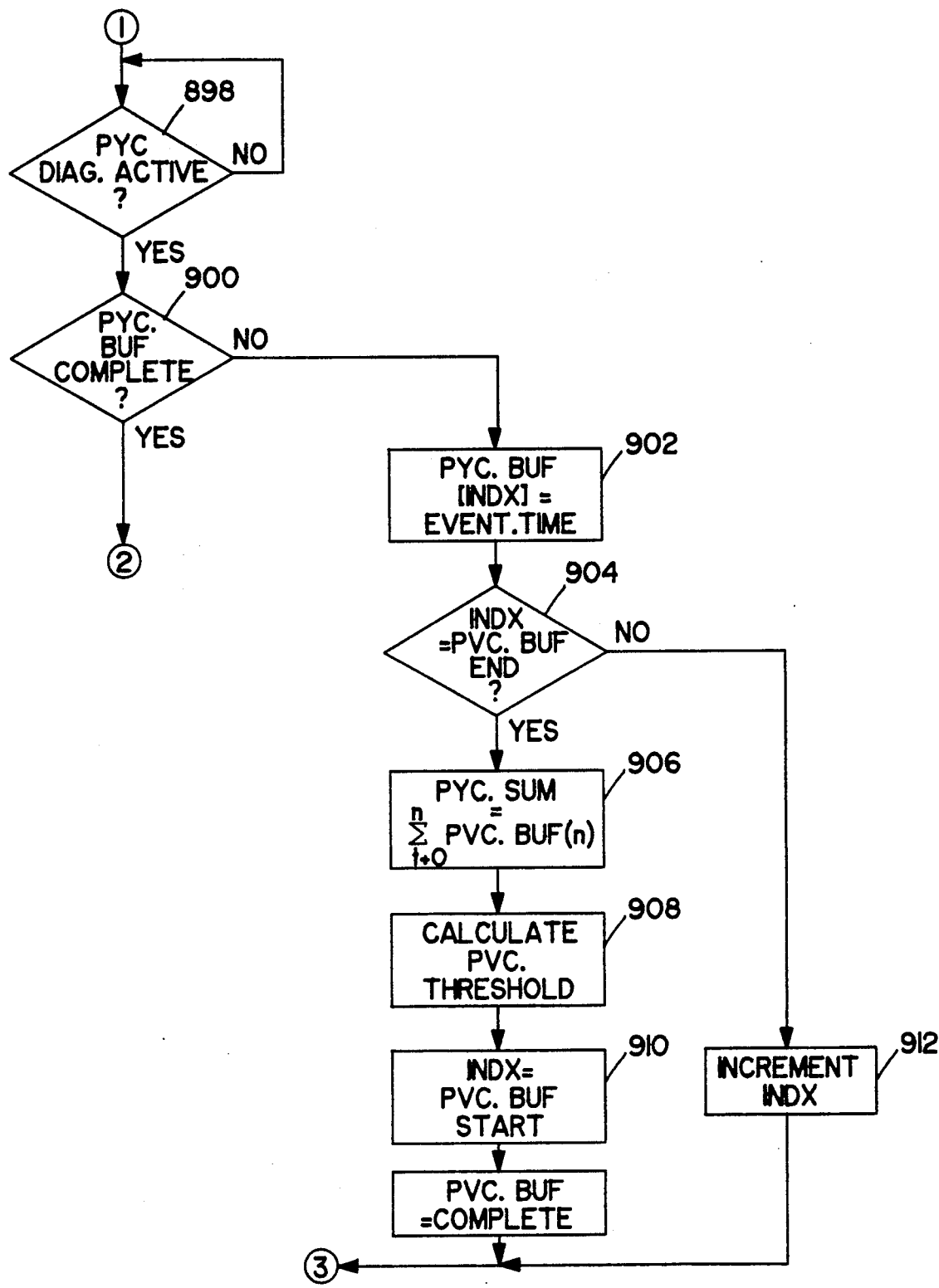
FIGS. 21-22 are simplified flowcharts of the PVC count and histogram diagnostic algorithm for storing data related to PVCs, couplets and runs as well as the time of overflow of a counter or histogram bin in memory register stages illustrated in FIG. 9 (Maps 1, 3-6).
Figure 22:
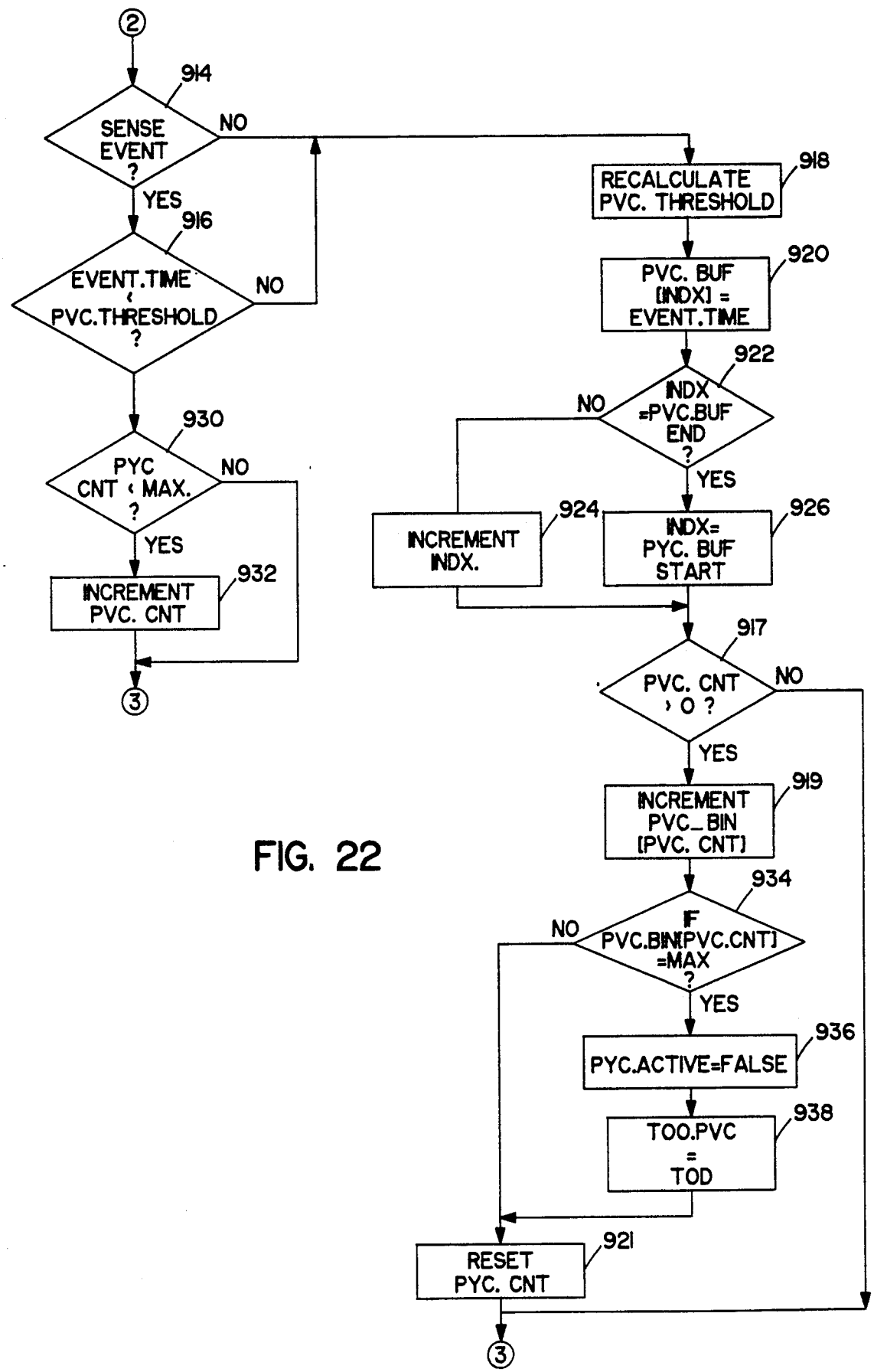

In the preferred embodiment, PVC counts and histogram bins are accommodated in the manner described in PART I. K. above. A simplified flow chart of the algorithms is depicted in FIGS. 21 and 22. The PVC-DTCT algorithm illustrated in FIG. 21 detects occurrences of PVCs by keeping a running average of the last eight rhythmic cycle lengths or intervals and comparing each new sense event elapsed time interval to a prematurity threshold elapsed time interval calculated as a programmable preactivity percentage of the average. The eight cycles include intervals ending with both paced events and sensed events outside the programmable refractory interval. The algorithm has a start-up operation whereby it initializes a running average and calculates the starting prematurity threshold.

In FIGS. 21 and 22, the EVENT.TIME is the elapsed interval. After initialization and establishment of the PVC.THRESHOLD timing window, any sensed event falling within the window will increment one of four 16-bit counters, (1) for counting single premature beats, (2) for counting two consecutive premature beats, (3) for counting three consecutive premature beats, (4) for counting four or more premature beats. If any of the counters overflow, the PVC bit of the overflow flag will be set, the time of overflow will be stored at TOO.PVC and all the PVC counters will be frozen.

At the outset in FIG. 21, decision block 898 tests to determine if the PVC diagnostic is ACTIVE and block 900 tests to determine if the PVC.BUF is complete at each paced and nonrefractory sensed event. If it is, then the algorithm moves to the start of the FIG. 22 flow chart. Assuming that PVC.BUF is not complete, then, in block 902, the EVENT.TIME is entered at the INDX pointer buffer location. If the INDX points to the last location, decision block 904 directs the summation of the EVENT.TIME values in block 906. The PVC.THRESHOLD is determined in block 908 in accordance with the formula:

*PVC. THRESHOLD=(PVC. SUM/PVC.BUF.SIZE)\*(PREMATURITY.FACTOR).*

Then the INDX pointer is set to the starting location in PVC.BUF in block 910 and the PVC.BUF is set to COMPLETE. If the INDX was not at the end as determined in block 904, then the INDX pointer is incremented in block 912.

In either case, once the PVC.BUF becomes filled up and the PVC.THRESHOLD is initialized in blocks 902-912, each succeeding event is thereafter examined in decision blocks 914 and 916 (FIG. 22) to determine if it is a sensed event and falls within the PVC.THRESHOLD. If so, the successive PVC counter (PVC.CNT) is incremented in block 932 unless it is determined to be at the count of 4. If not, a non-refractory or paced event has occurred, indicating that a potential run of PVCs has terminated.

The PVC.THRESHOLD is recalculated in block 918 using the formula:

PVC · THRESHOLD = ((PVC · SUM − PVC · BUF[INDX] + EVENT · TIME)/PVC · BUF · SIZE)*(PREMATURITY · FACTOR).

The current EVENT.TIME is then stored in the PVC.BUF in block 920. If the INDX pointer is at the end location of the buffer, the INDX is set to the start location of the circular buffer in block 926. Otherwise INDX is incremented in block 924.

Each time a PVC occurs, it increments the PVC.CNT in block 932. Unless it is already at "4" as determined in block 930. The particular 16-bit counter for 1, 2, 3, or 4 or more successive PVCs is incremented in block 919 depending on the number in the PVC.CNT when the next normal sensed or paced event occurs. A test is made at block 917 to determine if PVCs have occurred. The proper PVC.BIN is identified by using the value in PVC.CNT as an index into the PVC.BIN array as shown in block 919. A check is made at block 934 to determine if the currently selected PVC.BIN counter has reached its max value in which case the PVC.ACTIVE indicator is set to FALSE in block 936 and the time of overflow is stored in TOO.PVC at block 938. The PVC.CNT is then reset to zero in block 921 and the system is ready to process the next event.

Part XIII. Conclusion

The above described current event and counted event diagnostics represent a preferred embodiment of the inventions disclosed and claimed herein. Other diagnostics will suggest themselves in the context of one or more measured RCPs in single and dual climber multiprogrammable pacemakers.

For example, the activity and pressure sensors $S_1$, and $S_2$ may be employed in other rate control algorithms which are suggested in the prior art. The pressure sensor lends itself to measuring other RCPs, e.g. ejection time as suggested in U.S. Pat. No. 4,730,619 and peak and dP/dt blood pressures as suggested in U.S. Pat. No. 4,566,456. In the context of the present invention current values and counted events (including counts and histograms) of these parameters in combination with the time of overflow, projected and actual rate levels, and other features of the present invention would be feasible.

Certain of the above described diagnostics, e.g. the pulse width and pulse amplitude changes, the sensor threshold analysis and the PVC, couplet, and run count histograms, may be implemented in single and dual chamber multiprogrammable pacemakers and pacemaker-cardioverters-defibrillators with or without the capability of measuring RCPs.

While there has been shown what is considered to be the preferred embodiment of the invention, it will be apparent that many changes and modifications may be made therein without departing from the essential spirit of the invention. It is intended, therefore, in the annexed claims to cover all such changes and modifications as may fall within the true scope of the inventions as claimed herein.

What is claimed is:

1. An implantable, rate responsive cardiac pacemaker comprising:
   means for determining an occurrence of selected cardiac events;
   means for detecting and processing a physiologic parameter;
   means for delivering pacing pulses at a selected pacing rate;
   means for varying the pacing rate as a function of a stored algorithm having at least one programmed-in rate responsive modifier value for setting the pacing rate in dependence upon the measured physiologic parameter and the occurrence of selected cardiac events;
   means for establishing at least one rate response algorithm modifier value;
   means for periodically optimizing the rate response algorithm modifier value to achieve a predetermined rate achievement criteria;
   means for transmitting signals representative of the optimized rate responsive modifier value and the programmed-in rate responsive modifier value to a remote location external of said implantable pacemaker;
   means for storing n periodic changes of the first rate response algorithm modifier value and a time of change of the response algorithm modifier value in n memory locations;
   means for transmitting the n periodic changes to said remote location and their corresponding times;
   means for sampling the varying pacing rate and storing rate trend data in memory over a predetermined time duration, said rate trend data indicative of a trend in said pacing rate;
   means for transmitting the rate trend data in conjunction with the algorithm modifier value to said remote location;
   means for deriving beat-by-beat averages of the pacing rate and percentage of paced values in a total of the spaced and sensed event intervals value over programmable time segments; and
   means for accumulating the derived rate averages and percentage paced values in memory over a predetermined duration in conjunction with storing the n periodic changes for subsequent transmission to said remote location.

2. An implantable, rate responsive cardiac pacemaker comprising:
   means for determining an occurrence of selected cardiac events;
   means for detecting and processing a physiologic parameter;
   means for delivering pacing pulses at a selected pacing rate;
   means for varying the pacing rate as a function of a stored algorithm having at least one programmed-in rate responsive modifier value for setting the pacing rate in dependence upon the measured physiologic parameter and the occurrence of selected cardiac events;
   means for establishing at least one rate response algorithm modifier value;
   means for periodically optimizing the rate response algorithm modifier value to achieve a predetermined rate achievement criteria;
   means for transmitting signals representative of the optimized rate responsive modifier value and the programmed-in rate responsive modifier value to a remote location external of said implantable pacemaker;
   means for storing n periodic changes of the first rate response algorithm modifier value and a time of change of the response algorithm modifier value in n memory locations;
   means for transmitting the n periodic changes to said remote location and their corresponding times;
   means for selectively disabling said means for varying the pacing rate, and for operating said pacemaker at a further defined fixed or varying pacing rate;
   means for deriving a projected pacing rate as a function of said stored algorithm and storing projected rate trend data in memory over a predetermined time duration, said rate trend data indicative of a trend in said pacing rate; and
   means for transmitting the projected rate trend data in conjunction with the algorithm modifier value to said remote location.

3. The pacemaker of claim 2 further comprising:
   means for deriving beat-by-beat averages of the pacing rate and percentage of paced values in a total of the paced and sensed event intervals over programmable time segments; and
   means for accumulating the derived rate averages and percentage paced values in memory over a predetermined duration in conjunction with storing the n periodic changes for subsequent transmission to said remote location.

4. An implantable, rate responsive cardiac pacemaker comprising:
   means for determining an occurrence of selected cardiac events;
   means for detecting and processing a physiologic parameter;
   means for delivering pacing pulses at a selected pacing rate;
   means for varying the pacing rate as a function of a stored algorithm having at least one programmed-in algorithm modifiers rate responsive modifier value for setting the pacing rate in dependence upon the measured physiologic parameter and the occurrence of selected cardiac events;
   modifier value establishing means for establishing at least one rate response algorithm modifier value;
   means for periodically optimizing the rate response algorithm modifier value to achieve a predetermined rate achievement criteria; and,
   means for transmitting signals representative of the optimized rate responsive modifier value and the programmed-in rate responsive modifier value to a remote location external of said implantable pacemaker;

wherein said means for detecting and processing a physiologic parameter further comprises:

first sensor and signal processing means for deriving a first physiologic signal representative of a cardiac function; and second sensor and signal processing means for deriving a second physiologic signal representative of a metabolic demand for cardiac output;

and wherein said means for varying the pacing rate further comprises means for selectively employing either or both of the first and second physiologic signals to derive a pacing rate;

and wherein said modifier value establishing means further comprises means for establishing first and second gain control values and a relative weighting coefficient for said first and second physiologic signals; and further comprising:

means for deriving a pacing rate as a function of the first and/or second physiologic signals modified by said gain control values and weighting coefficient;

and wherein said optimizing means periodically optimizes the gain control values and weighting coefficient.

5. The pacemaker of claim 4 further comprising:

means for storing n periodic changes, achieved by said optimizing means, of the first and second gain control values and the weighting coefficient, and a corresponding rate of said n changes in n memory locations; and means for transmitting data representing the n periodic changes to said remote location along with the dates that the changes were made.

6. The pacemaker of claim 5 further comprising:

means for sampling the varying pacing rate and storing rate trend data in memory over a predetermined time duration, said rate trend data indicative of a trend in said pacing rate; and means for transmitting the rate trend data in conjunction with the n periodic changes data to said remote location.

7. The pacemaker of claim 6 further comprising:

means for deriving beat-by-beat averages of the pacing rate and percentage of paced to total paced and sensed event intervals value over programmable time segments; and means for accumulating the derived rate averages and percentage paced values in memory over a predetermined duration in conjunction with storing the n periodic changes data for subsequent transmission to said remote location.

8. The pacemaker of claim 5 further comprising:

means for selectively disabling said means for varying the pacing rate and operating said pacemaker at a further defined fixed or varying pacing rate;

means for deriving the projected pacing rate as a function of said stored algorithm and storing projected rate trend data in memory over a predetermined time duration; and means for transmitting the projected rate trend data in conjunction with the n periodic changes data to said remote location.

9. The pacemaker of claim 8 further comprising:

means for deriving beat-by-beat averages of the projected pacing rate over programmable time segments; and means for accumulating the derived rate averages in memory over a predetermined duration in conjunction with storing the n periodic changes data for subsequent transmission to said remote location.

10. An implantable, programmable cardiac pacemaker comprising:

means for determining an occurrence of selected cardiac paced and sensed events;

means for delivering pacing pulses at a predetermined pacing rate corresponding to an interval elapsed from a preceding paced or sensed event;

means for measuring a predetermined parameter associated with each one of said selected cardiac events;

means for registering occurrences of said selected cardiac events;

means for classifying each said registered event into respective classes of said parameter associated with said event in accordance with a measured value of said parameter;

means for accumulating counts of said registered events for each said class thereby providing data of a distribution of said registered events;

means for halting accumulating of said counts of said registered events upon achievement of a predetermined count of said registered events for at least one of said classes and registering a time corresponding to the achievement of the maximum count in association with the specific register; and means for outputting signals representative of said accumulated counts and said time to a location external of said implantable pacemaker.

11. The cardiac pacemaker of claim 10 further comprising:

means for varying the pacing rate as a function of a physiologic parameter of the patient;

means for classifying each of said pacing rates into respective rate classes between a maximum and a minimum allowable rate, whereby histograms of the rate data are accumulated in said accumulating means until the count in one of said respective rate classes achieves a predetermined maximum count;

means for registering a time of achievement of the maximum count; and means for outputting signal representative of the histograms and said time to said external location.

12. The cardiac pacemaker of claim 10 further comprising:

means for counting selected sensed events and for classifying each of said sensed events into respective interval classes between a maximum and a minimum allowable interval whereby histograms of the sensed event interval data are accumulated in said accumulating means until the count in one of said respective interval classes achieves a predetermined maximum count;

means for registering a time corresponding to the achievement of the maximum count; and means for outputting signal representative of the histograms and said time to said external location.

13. A method for providing an optimized pacing rate of stimulation pulses in a rate responsive cardiac pacemaker, as a function of at least one selected rate control parameter, each of said rate control parameters having a value which varies as a function of changes in a patient's physiologic demand for cardiac output, the method comprising the steps of:

sensing each of said rate control parameter values and for providing a sensor output representative thereof;

deriving desired pacing rates for each of said sensor means as a function of said sensor output signals corresponding thereto, modified by a predetermined rate response algorithm modifier function for each of said sensor means, such that for a predetermined change in sensor output signal a corresponding change in said desired pacing rate is provided;

periodically monitoring a relationship between each of said derived desired pacing rates and a defined achievement criterion corresponding thereto over a predetermined optimization period, for providing an achievement output indicative of each of said monitored relationships, wherein each of said achievement criterion is reflective of expected levels of exercise of said patient during said optimization period;

providing optimized pacing rates as a function of each of said derived desired pacing rates;

adjusting each of said rate response algorithm modifier functions as a function of said achievement output corresponding thereto, such that each of said adjusted rate response functions provides an increased or decreased change in desired pacing rate corresponding to said predetermined change in sensor output;

storing in memory, said rate response algorithm modifier functions adjusted during the optimization periods; and upon receipt of an interrogation command, transmitting the stored functions to a remote location.

* * * * *